(12) United States Patent
Schmidt et al.

(10) Patent No.: US 7,534,372 B2
(45) Date of Patent: May 19, 2009

(54) CATALYTIC PARTIAL OXIDATION OF HYDROCARBONS

(75) Inventors: Lanny D. Schmidt, Minneapolis, MN (US); Jakob J. Krummenacher, Minneapolis, MN (US); Kevin N. West, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 11/880,745

(22) Filed: Jul. 24, 2007

(65) Prior Publication Data

US 2007/0293713 A1    Dec. 20, 2007

Related U.S. Application Data

(62) Division of application No. 10/620,183, filed on Jul. 15, 2003, now Pat. No. 7,262,334.

(60) Provisional application No. 60/426,328, filed on Nov. 13, 2002.

(51) Int. Cl.
*C01B 3/26* (2006.01)
(52) U.S. Cl. ..................... 252/373
(58) Field of Classification Search ............... 252/373
See application file for complete search history.

(56) References Cited

U.S. PATENT DOCUMENTS

| | | | |
|---|---|---|---|
| 2,776,195 A * | 1/1957 | Wessolek ............ 48/215 |
| 3,900,646 A | 8/1975 | Clyde | |
| 3,917,468 A * | 11/1975 | Van den Berg et al. .... 48/199 R |
| 3,957,685 A | 5/1976 | Heide et al. | |
| 3,998,758 A | 12/1976 | Clyde | |
| 4,088,607 A | 5/1978 | Weidenbach et al. | |
| 4,251,239 A | 2/1981 | Clyde et al. | |
| 4,253,302 A | 3/1981 | Asano et al. | |
| 4,308,233 A | 12/1981 | Narumiya et al. | |
| 4,568,595 A | 2/1986 | Morris | |

(Continued)

FOREIGN PATENT DOCUMENTS

CA    2323728 A1    4/2001

(Continued)

OTHER PUBLICATIONS

Aupretre et al., "Le vaporeformage catalytique: Application a la production embarquee d'hydrogene a partir d'hydrocarbures ou d'alcools," *Ann. Chim. Sci. Mat.*, 2001, 26(4):93-106 (with English language abstract).

(Continued)

*Primary Examiner*—Wayne Langel
(74) *Attorney, Agent, or Firm*—Mueting Raasch & Gebhardt, P.A.

(57) ABSTRACT

A process for the production of a reaction product including a carbon containing compound. The process includes providing a film of a fuel source including at least one organic compound on a wall of a reactor, contacting the fuel source with a source of oxygen, forming a vaporized mixture of fuel and oxygen, and contacting the vaporized mixture of fuel and oxygen with a catalyst under conditions effective to produce a reaction product including a carbon containing compound. Preferred products include α-olefins and synthesis gas. A preferred catalyst is a supported metal catalyst, preferably including rhodium, platinum, and mixtures thereof.

19 Claims, 14 Drawing Sheets

U.S. PATENT DOCUMENTS

| | | | |
|---|---|---|---|
| 4,810,685 A | 3/1989 | Twigg et al. | |
| 4,863,712 A | 9/1989 | Twigg et al. | |
| 4,940,826 A | 7/1990 | Font Freide et al. | |
| 5,105,052 A | 4/1992 | Font Freide et al. | |
| 5,221,464 A | 6/1993 | Durante et al. | |
| 5,382,741 A | 1/1995 | Astbury et al. | |
| 5,500,149 A | 3/1996 | Green et al. | |
| 5,593,935 A | 1/1997 | Golunski et al. | |
| 5,597,771 A | 1/1997 | Hu et al. | |
| 5,639,929 A | 6/1997 | Bharadwaj et al. | |
| 5,648,582 A | 7/1997 | Schmidt et al. | |
| 5,654,491 A | 8/1997 | Goetsch et al. | |
| 5,663,473 A | 9/1997 | Griffiths et al. | |
| 5,856,585 A | 1/1999 | Sanfilippo et al. | |
| 5,905,180 A | 5/1999 | Yokoyama et al. | |
| 5,980,731 A | 11/1999 | Kao et al. | |
| 5,980,782 A | 11/1999 | Hershkowitz et al. | |
| 5,993,192 A | 11/1999 | Schmidt et al. | |
| 6,072,097 A | 6/2000 | Yokoyama et al. | |
| 6,083,425 A | 7/2000 | Clawson et al. | |
| 6,092,921 A | 7/2000 | Wentinck et al. | |
| 6,123,913 A | 9/2000 | Clawson et al. | |
| 6,126,908 A | 10/2000 | Clawson et al. | |
| 6,197,717 B1 | 3/2001 | Alexander et al. | |
| 6,207,122 B1 | 3/2001 | Clawson et al. | |
| 6,221,280 B1 | 4/2001 | Anumakonda et al. | |
| 6,245,303 B1 | 6/2001 | Bentley et al. | |
| 6,254,807 B1 | 7/2001 | Schmidt et al. | |
| 6,254,839 B1 | 7/2001 | Clawson et al. | |
| 6,365,543 B1 | 4/2002 | Schmidt et al. | |
| 6,387,554 B1 | 5/2002 | Verykios | |
| 6,407,301 B1 | 6/2002 | Foley et al. | |
| 6,436,363 B1 | 8/2002 | Hwang et al. | |
| 6,444,867 B1 | 9/2002 | Samsel et al. | |
| 6,452,061 B1 | 9/2002 | Schmidt et al. | |
| 6,455,597 B2 | 9/2002 | Hohn et al. | |
| 6,506,359 B1 | 1/2003 | Maruko | |
| 6,548,447 B1 | 4/2003 | Yokoyama et al. | |
| 6,605,376 B2 | 8/2003 | Verykios | |
| 6,852,307 B1* | 2/2005 | Kuipers et al. | 423/651 |
| 6,884,368 B2* | 4/2005 | Zhdanok et al. | 252/373 |
| 7,255,848 B2* | 8/2007 | Deluga et al. | 423/648.1 |
| 7,262,334 B2 | 8/2007 | Schmidt et al. | |
| 2001/0009653 A1 | 7/2001 | Clawson et al. | |
| 2001/0027258 A1 | 10/2001 | Hohn et al. | |
| 2002/0009408 A1 | 1/2002 | Wieland et al. | |
| 2002/0087042 A1 | 7/2002 | Schmidt et al. | |
| 2003/0060364 A1 | 3/2003 | Anzai et al. | |
| 2004/0014600 A1 | 1/2004 | Fukunaga | |
| 2004/0199038 A1 | 10/2004 | Schmidt et al. | |
| 2006/0014840 A1 | 1/2006 | Schmidt et al. | |

FOREIGN PATENT DOCUMENTS

| | | |
|---|---|---|
| EP | 0303439 A2 | 2/1989 |
| EP | 0576096 A2 | 12/1993 |
| EP | 0640559 A1 | 3/1995 |
| EP | 1043271 A1 | 10/2000 |
| EP | 0922011 B1 | 7/2001 |
| EP | 1118583 A2 | 7/2001 |
| EP | 1109876 B1 | 7/2003 |
| EP | 1007472 B1 | 9/2003 |
| FR | 1379027 | 11/1964 |
| GB | 1067957 | 5/1967 |
| JP | 2001-080904 | 3/2001 |
| JP | 2001-089108 | 4/2001 |
| WO | WO 96/13475 | 5/1996 |
| WO | WO 96/33149 | 10/1996 |
| WO | WO 97/26987 | 7/1997 |
| WO | WO 97/29062 | 8/1997 |
| WO | WO 98/08771 | 3/1998 |
| WO | WO 99/35082 | 7/1999 |
| WO | WO 99/61369 | 12/1999 |
| WO | WO 00/14180 | 3/2000 |
| WO | WO 01/32556 A1 | 5/2001 |

OTHER PUBLICATIONS

Bcal, "News: Team engineers hydrogen from biomass" [online]. University of Wisconsin-Madison, Aug. 28, 2002 [retrieved on Oct. 24, 2005]. Retrieved from the Internet:<URL:http:www.news.wisc.edu/story.php?gct=7766>; 2 pgs.

Bodke et al., "The Effect of Ceramic Supports on Partial Oxidation of Hydrocarbons Over Noble Metal Coated Monoliths," *Journal of Catalysis*, Oct. 1998;179:138-149.

Bodke et al., "High Selectivities to Ethylene by Partial Oxidation of Ethane," *Science*, Jul. 1999; 285:712-715.

Bodke et al., "Oxidative Dehydrogenation of Ethane at Millisecond Contact Times: Effect of $H_2$ Addition," *J. Catalysis*, Apr. 2000; 191:62-74.

Brown, "A comparative study of fuels for on-board hydrogen production for fuel-cell-powered automobiles," *Int. J. Hydrogen Energy*, Apr. 2001, 26:381-397.

Burch et al., "Investigation of the reactions of acetaldehyde on promoted rhodium catalysts," *Applied Catalysis A: General*, Sep. 1992; 88:61-76.

Cavallaro et al., "Ethanol steam reforming in a molten carbonate fuel cell. A preliminary kinetic investigation," *Int. J. Hydrogen Energy*, Jun. 1996; 21(6):465-469.

Cavallaro, "Ethanol Steam Reforming on $Rh/Al_2O_3$ Catalysts," *Energy & Fuels*, 2000, 14:1195-1199. Published on Web Sep. 16, 2000.

Chornet et al., "Harnessing hydrogen," *Nature*, Aug. 29, 2002; 418:928-929.

Cohn et al., "Onboard plasmatron generation of hydrogen for extremely low emission vehicles with internal coombustion engines," *Int. J. Vehicle Design*, 1996; 17(5/6):550-561.

Cordi et al., "Transient oxidation of volatile organic compounds on a $CuO/Al_2O_3$ catalyst," *Applied Catalysis B: Environmental*, Dec. 1997; 14:23-36.

Cortright et al., "Hydrogen from catalytic reforming of biomass-derived hydrocarbons in liquid water," *Nature*, Aug. 29, 2002; 418:964-967.

Deluga et al., "Renewable Hydrogen from Ethanol by Autothermal Reforming," *Science*, Feb. 2004; 303:993-997.

Dietz III et al., "Partial Oxidation of $C_5$ and $C_6$ Alkanes over Monolith Catalysts at Short Contact Times," *Journal of Catalysis*, Jun. 1998; 176:459-473.

Fatsikostas et al., "Steam reforming of biomass-derived ethanol for the production of hydrogen for fuel cell applications," *Chem. Comm.*, 2001; 851-852. First Published as an Advance Article on the Web, Apr. 18, 2001.

Fishtik et al., "A thermodynamic analysis of hydrogen production by steam reforming of ethanol via response reactions," *Int. J. Hydrogen Energy*, Jan. 2000; 25:31-45.

Freni, "Rh based catalysts for indirect internal reforming ethanol applications in molten carbonate fuel cells," *Journal of Power Sources*, Feb. 2001; 94:14-19.

Galvita et al., "Synthesis gas production by steam reforming of ethanol," *Applied Catalysis A: General*, Oct. 2001; 220:123-127.

Goetsch et al., "Microsecond Catalytic Partial Oxidation of Alkanes," *Science*, Mar. 1996; 271:1560-1562.

Gomez et al., "Kinetic Study of Partial Oxidation of Ethanol over VMgO Catalyst," *Ind. Eng. Chem. Res.*, 1997; 36:3468-3472. Abstract published in Advance ACS Abstracts, Jul. 15, 1997.

Hacohen et al., "Driving Cycle Simulation of a Vehicle Motored by a SI Engine Fueled with $H_2$-Enriched Gasoline," *Int. J. of Hydrogen Energy*, 1991; 16(10):695-702.

Henning et al., "Oxidative dehydrogenation of ethane at short contact times: species and temperature profiles within and after the catalyst." *Chem. Eng. Sci.*, Jul. 2002; 57(14):2615-2625.

Hickman et al., "Synthesis gas formation by direct oxidation of methane over Pt monoliths," *Journal of Catalysis*, Nov. 1992; 138:267-82.

Hickman et al., "Synthesis Gas Formation by Direct Oxidation of Methane over Rh Monoliths," *Catal. Lett.*, Sep. 1993; 17(3-4):223-237.

Hickman et al., "Production of syngas by direct catalytic oxidation of methane," *Science*, Jan. 15, 1993; 259:343-346.

Hickman et al., "Steps in $CH_4$ Oxidation on Pt and Rh Surfaces: High-Temperature Reactor Simulations," *AIChE Journal*, Jul. 1993; 39(7):1164-1177.

"Homogenous-heterogeneous combustion: Thermal and chemical coupling," Abstract, DOE Contract No. FG02-88ER13878, 2 pgs. Jan. 1992.

Huff et al., "Partial Oxidation of $CH_4$, $C_2H_6$, and $C_3H_8$ on Monoliths at Short Contact Times," *Stud. Surf. Sci. Catal.*, Natural Gas Conversion II, Proceedings of the Third Natural Gas Conversion Symposium, Sydney, Australia, Jul. 4-9, 1993; 81:315-320 (1994).

Ioannides, "Thermodynamic analysis of ethanol processors for fuel cell applications," *Journal of Power Sources*, Jan. 2001, 92:17-25.

Jamal et al., "On-Board Generation of Hydrogen-Rich Gaseous Fuels—A Review," *Int. J. Hydrogen Energy*, Jul. 1994; 19(7):557-572.

Klein et al., "Catalytic partial oxidation of methane to syngas: staged and stratified reactors with steam addition," *Stud. Surf. Sci. Catal.*, Natural Gas Conversion VI, Proceedings of the Sixth Natural Gas Conversion Symposium, Alaska, Jun. 17-22, 2001; 136:245-250 (2001).

Krummenacher et al., "Catalytic partial oxidation of higher hydrocarbons at millisecond contact times: decane, hexadecane, and diesel fuel," *Journal of Catalysis*, Apr. 2003;215:332-343.

Krummenacher et al., "Catalytic Partial Oxidation of Higher Hydrocarbons at Millisecond Contact Tiems: Decane, Hexadecane, and Diesel Fuel," 18th North American Catalysis Society Meeting, Cancun, Mexico, Jun. 1-6, 2003; 2 pgs.

Lakshmi et al., "Synthesis, Characterization, and Activity Studies of Vanadia Supported on Zirconia and Phosphorus-Modified Zirconia," *Langmuir*, 1999; 15:3521-3528. Published on the Web Apr. 24, 1999.

"Lightweight Valve Train Materials," Report based on research conducted under DOE Cooperative Agreement DE-FC05-97OR22579, U.S. Dept. of Energy, Metals and Ceramics Division, Heavy Vehicle Propulsion Materials Program Quarterly Progress Report, Oak Ridge National Laboratory, Oak Ridge, TN (Jan.-Mar. 2005) 10 pages.

Mariño et al., "Hydrogen from steam reforming of ethanol. Characterization and performance of copper-nickel supported catalysts," *Int. J. Hydrogen Energy*, Dec. 1998;23(12):1095-1101.

Mariño et al., "Hydrogen production from steam reforming of bioethanol using $Cu/Ni/K/\gamma$-$Al_2O_3$ catalysts. Effect of Ni," *Int. J. Hydrogen Energy*, Jul. 2001, 26:665-668.

Mazzocchia et al., "Hydrogenation of CO over $ZrO_2$-supported Rh catalysts: kinetic aspects," *Journal of Molecular Catalysis*, Jul. 1990; 60:283-294.

Mazzocchia et al., "Hydrogenation of CO over $Rh/Sio_2$-$CeO_2$ catalysts: kinetic evidences," *Journal of Molecular Catalysis A: Chemical*, Jan. 2001; 165:219-230.

O'Connor et al., "High yields of synthesis gas by millisecond partial oxidation of higher hydrocarbons," *Catal. Lett.*, Dec. 2000; 70:99-107.

Otsuka et al., "The Partial Oxidation of Light Alkanes ($CH_4$, $C_2H_6$, $C_3H_8$) Over B-P Mixed Oxides," *Stud. Surf. Sci. Catal.*, Natural Gas Conversion, Proceedings of the Natural Gas Conversion Symposium, Oslo, Aug. 12-17, 1990; 61:15-23 (1991).

Pestryakov et al., "Physicochemical study of active sites of metal catalysts for alcohol partial oxidation," *Journal of Molecular Catalysis A: Chemical*, Sep. 2000, 158:325-329.

Rampe et al., "Hydrogen generation from biogenic and fossil fuels by autothermal reforming," *Journal of Power Sources*, Mar. 2000; 86:536-541.

Su et al., "Heterogeneous Partial Oxidation of Light Alkanes," Abstracts of Papers, 224th ACS National Meeting, Boston, MA, Aug. 18-22, 2002; 3 pgs.

Tamman et al., "Zur Rekristallisation von Metallen und Salzen," *Zeitschrift für Anorganische und Allgemeine Chemie*, 1923; 126:119-128, and English translation. (22 pages total).

Traxel et al., "Partial Oxidation of methanol at millisecond contact times," *Applied Catalysis A: General*, May 2003; 244:129-140.

Tsiakaras et al., "Thermodynamic analysis of a solid oxide fuel cell system fuelled by ethanol," *Journal of Power Sources*, Dec. 2001, 102:210-217.

Vasudeva et al., "Steam reforming of ethanol for hydrogen production: thermodynamic analysis," *Int. J. Hydrogen Energy*, Jan. 1996; 21(1):13-18.

Vickers et al., "Plot Column Considerations for the Gas Chromatographic Analysis of Ozone Precursors," *J&W Scientific*, Aug. 1998:9 pgs.

Wang et al., "Study on the partial oxidation of ethanol to hydrogen in the presence of Ni-Fe catalyst," *Wuii Huaxue Xuebao (Acta Physico-Chimica Sinica)*, 2002, 18(5):426-431; with English language abstract and translation, 12 pgs.

* cited by examiner

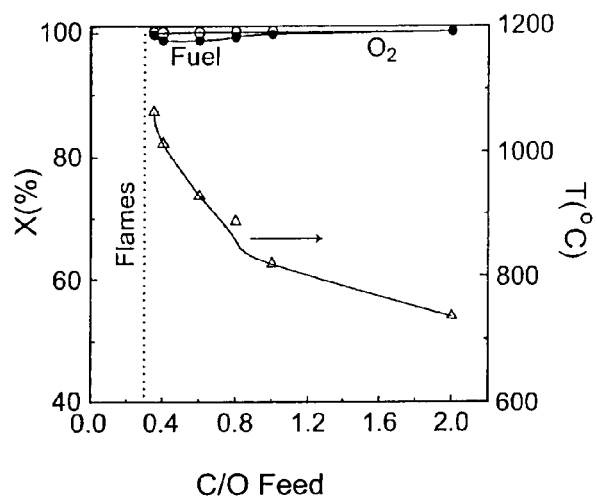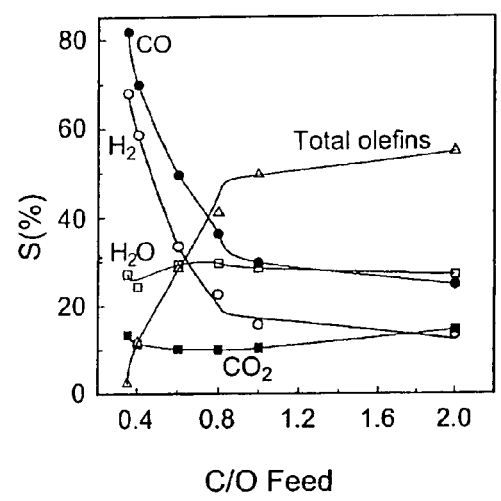
Fig. 13A
Fig. 13B

US 7,534,372 B2

CATALYTIC PARTIAL OXIDATION OF HYDROCARBONS

CONTINUING APPLICATION DATA

This application is a divisional application of U.S. patent application Ser. No. 10/620,183, filed on Jul. 15, 2003, which claims the benefit of U.S. Provisional Application Ser. No. 60/426,328, filed Nov. 13, 2002, both of which are incorporated herein in their entireties by reference.

STATEMENT OF GOVERNMENT RIGHTS

The present invention was made with support by the ARL Collaborative Technology Alliance in Power and Energy, Cooperative Agreement No. DAAD19-01-2-0010; U.S. Army Grant #DAAD19-00-R-0005; and Department of Energy Grant #DE-FC05-97OR22579. The United States government has certain rights in the invention.

BACKGROUND

Reforming hydrocarbons is important in many applications to produce fuels such as $H_2$ and chemical intermediates such as synthesis gas (syngas), and olefins. Reforming has generally been accomplished either by steam reforming or steam cracking which involve reaction with $H_2O$ in endothermic processes or by partial oxidation, which involves reaction with $O_2$ in exothermic processes. Conversion of methane to syngas by both processes is well established, and reactions of alkanes up to iso-octane have been demonstrated.

While steam reforming and steam cracking of higher alkanes, such as diesel fuel, can be accomplished under suitable conditions, the partial oxidation of higher alkanes presents several problems, such as flames during vaporization and mixing, soot formation associated with combustion of fuel-rich gases, and coke formation on reactor walls and on catalysts.

Currently there is considerable interest in reforming logistic fuels such as diesel and JP-8 (similar to kerosene and used as a military fuel) into light alkanes and especially $H_2$ for devices such as fuel cells, which function either exclusively on $H_2$ (the proton exchange membrane fuel cell) or which function best with $H_2$ in the fuel (the solid oxide fuel cell). Since a major interest is in fuel cells for transportation vehicles, gasoline and diesel are essential fuels in the next generation of fuel cell vehicles.

There is also considerable interest in fuel reforming for pollution abatement in automotive applications with internal combustion engines. Reforming of gasoline or diesel into $H_2$ and other small molecules creates a fuel that burns very efficiently, thus reducing or eliminating exhaust emissions of hydrocarbons, CO, and particulate matter. The abatement of $NO_x$ in diesel engines is especially difficult because, unlike a spark ignited gasoline engine in a lean burn environment there is insufficient $H_2$, CO, and small hydrocarbons to react with $NO_x$ in the catalytic converter. Therefore, reforming part of the fuel and using it to react with $NO_x$ could be important in diesel emissions control.

There is a need in the art for a convenient and scalable process for the conversion of hydrocarbon fuels including alkanes, particularly higher alkanes, cyclic alkanes, and aromatics, which provide valuable intermediates and products, such as synthesis gas and α-olefins with relatively high selectivities.

SUMMARY OF THE INVENTION

The present invention provides a process for the production of a compound including carbon, the process including: providing a fuel source including at least one organic compound, preferably a hydrocarbon, and more preferably a liquid hydrocarbon, to a reactor; forming a film of the fuel source on a wall of the reactor; providing a source of oxygen including molecular oxygen to the reactor; contacting the fuel source with the source of oxygen; forming a vaporized mixture of fuel and oxygen; then contacting the vaporized mixture of fuel and oxygen with a catalyst under conditions effective to produce a reaction product including a carbon containing compound.

As used herein, an "organic compound" includes, but is not limited to, a hydrocarbon compound with optional elements other than carbon and hydrogen, such as oxygen, nitrogen, sulfur, and silicon, that is classified as an aliphatic compound, cyclic compound, or combination of aliphatic and cyclic groups (e.g., alkaryl and aralkyl groups) within any one compound. The term "aliphatic compound" means a saturated or unsaturated linear or branched hydrocarbon compound. This term is used to encompass alkanes, alkenes, and alkynes, for example.

The term "cyclic compound" means a closed ring hydrocarbon compound that is classified as an alicyclic, aromatic, or heterocyclic compound. The term "alicyclic compound" means a cyclic hydrocarbon having properties resembling those of aliphatic compounds. The term "aromatic compound" or "aryl compound" means a mono- or polynuclear aromatic hydrocarbon. The term "heterocyclic compound" means a closed ring hydrocarbon in which one or more of the atoms in the ring is an element other than carbon (e.g., nitrogen, oxygen, sulfur, etc.).

Additionally, organic compounds of the present invention may be substituted with, but not limited to, O, N, Si, or S atoms, for example, in the chain (as in an alkoxy group) as well as carbonyl groups or other conventional substitution.

As used herein, a "carbon containing compound" includes both organic and inorganic compounds that include carbon atoms. Furthermore, a carbon containing compound may additionally include elements other than carbon, such as, but not limited to, hydrogen, oxygen, nitrogen, silicon, and sulfur, for example. A carbon containing compound as used herein preferably does not include significant amounts of coke. Coke is understood in the art to be the solid residue containing 90-98% carbon which results from heating coal in the absence of air.

While this process is suitable for use with any fuel source of the present invention, preferably the fuel source includes at least one hydrocarbon of any size. Advantageously, the present invention provides the ability to safely and effectively react larger hydrocarbons, such as hydrocarbons having at least 6 carbon atoms, with an oxygen source and a catalyst to provide products including carbon containing compounds. Products that may advantageously be produced by processes of the present invention include, but are not limited to, alkenes, preferably α-olefins, and synthesis gas.

In another embodiment of the present invention, a process for the production of an alkene is provided, the process including: providing a fuel source including at least one liquid hydrocarbon; providing at least one source of oxygen including molecular oxygen; delivering the fuel source to a reactor including a wall; forming a film of the fuel source on the reactor wall; contacting the fuel source with the source of oxygen; forming a vaporized mixture of fuel and oxygen; and contacting the vaporized mixture of fuel and oxygen with a catalyst under conditions effective to produce a reaction product including an alkene.

In yet another embodiment of the present invention, a process for the production of an α-olefin is provided, the process including: providing a fuel source including at least one liquid n-alkane; providing at least one source of oxygen including molecular oxygen; delivering the fuel source to a reactor including a wall; forming a film of the fuel source on the reactor wall; contacting the fuel source with the source of oxygen; forming a vaporized mixture of fuel and oxygen; and contacting the vaporized mixture of fuel and oxygen with a catalyst under conditions effective to produce a reaction product including an α-olefin.

In a further embodiment of the present invention, a process for the production of synthesis gas is provided, the process including: providing a fuel source including at least one liquid hydrocarbon; providing at least one source of oxygen including molecular oxygen; delivering the fuel source to a reactor including a wall; forming a film of the fuel source on the reactor wall; contacting the fuel source with the source of oxygen; forming a vaporized mixture of fuel and oxygen; and contacting the vaporized mixture of fuel and oxygen with a catalyst under conditions effective to produce a reaction product including synthesis gas.

BRIEF DESCRIPTION OF THE DRAWINGS

FIGS. 13A and 13B. Graphs indicting the effect of the feed ratio on the partial oxidation of diesel fuel (fuel and oxygen conversions, the back face temperature, and product selectivities, Figs. A and B, respectively) at 2 standard liters per minute using a washcoated rhodium coated alumina ceramic foam monolith catalyst.

DETAILED DESCRIPTION OF PREFERRED EMBODIMENTS

Figure 1B:
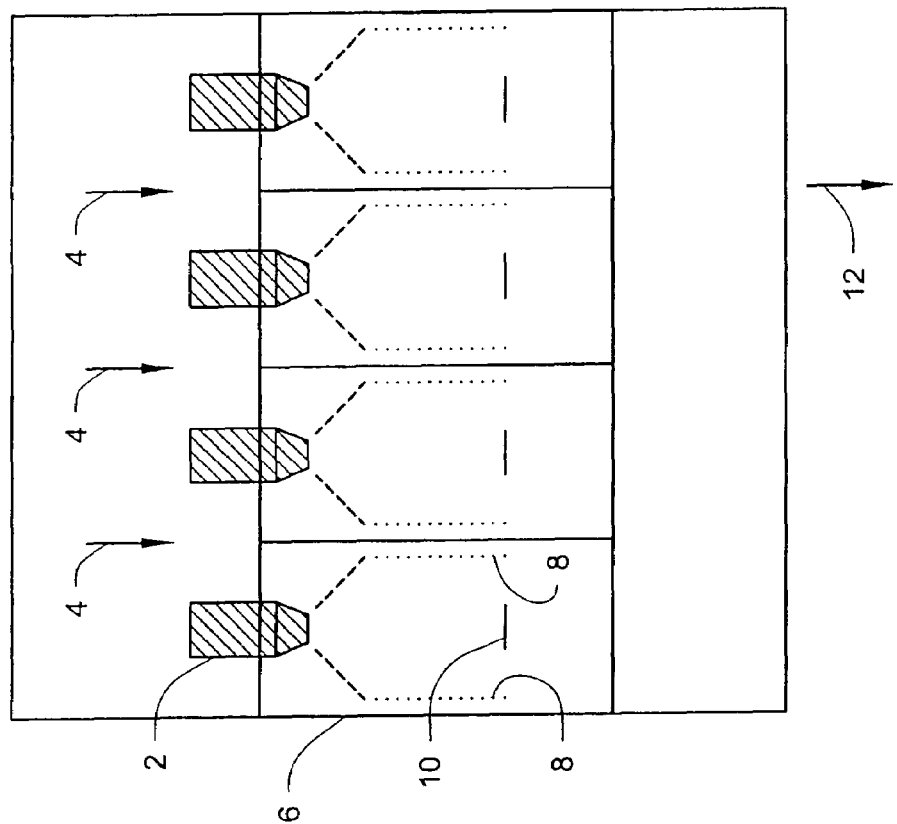
FIGS. 1A and 1B. Diagram of a vaporization array, plan view (A) and cross sectional view (B).

The present invention is directed to a process for the catalytic partial oxidation of a fuel source including at least one organic compound that is mixed with a source of oxygen and contacted with a catalyst. Preferably, the organic compound is a hydrocarbon, and more preferably, a liquid hydrocarbon. Preferably, the method uses an evaporator mixer system under conditions effective to produce a reaction product including a carbon-containing compound.

Preferred products include alkenes, preferably α-olefins, and synthesis gas (also known as syngas, which is $H_2$ and CO), and are preferably provided in millisecond contact times with the catalyst. The process may be designed or "tuned" (that is, reaction conditions, such as carbon to oxygen ratios, flow rates, etc., may be selected to provide the desired product, such as an alkene vs. syngas) to provide short chain alkenes, preferably ethylene and propylene, longer chain alkenes, preferably α-olefins, and synthesis gas at relatively high selectivities.

Additionally, the present processes are scalable, suitable for production of energy, for example watts of energy that hydrogen produces when put through a fuel cell, of from about 20 watts up to megawatts of product. While the processes of the present invention are suitable for use with reactants of various sizes, including methane and lighter alkanes, the present process is particularly advantageous in that larger hydrocarbons and mixtures of hydrocarbons may typically be used as starting materials.

A preferred process of the present invention includes an evaporator mixer system. This system includes an apparatus for delivery of the liquid fuel source, in the manner described below, to a reactor that includes walls that, preferably, have been heated to a temperature higher than the fuel boiling point. The fuel is delivered to the reactor by an apparatus that provides relatively small droplets of fuel, preferably at least about 25 micrometers in diameter, at a relatively low pressure, preferably at least about 3 psi (pounds per square inch; about 21 kilopascal), preferably no greater than about 7 psi (about 48 kilopascal). By delivery in this manner, a film of the liquid fuel is created on a wall of the reactor. This allows vaporization and mixing substantially simultaneously of the fuel source with the oxygen source, avoiding the combustion of reactants that can occur when fuel is vaporized before mixing with an oxygen source. The vaporization and mixing of the fuel source occurs instantly, for example in less than 10 milliseconds (ms), preferably less than 5 ms, and more preferably less than 1 ms. It then takes the vaporized and mixed fuel source and oxygen source approximately 10 to 20 ms, depending on the length of the reactor and the flow rate, to travel to the catalyst. Thus, by avoiding combustion, a safer reaction is provided and coking of the catalyst may be avoided. Also, by delivering the fuel in this manner, water, which can prevent combustion in the reaction, does not need to be added to the reaction (although for certain embodiments water can be added).

The processes of the present invention may preferably and advantageously be operated using a fuel to oxygen atomic ratio (C/O) of the fuel source and oxygen source that includes an excess of fuel as compared to typical known catalytic processes, for example, an internal combustion engine. An internal combustion engine, such as is used with an automobile, requires a C/O ratio of the fuel and oxygen source that is at or below the combustion stoichiometry for the fuel provided to improve engine performance and lower unwanted emissions. The processes of the present invention, however, preferably include C/O atomic ratios of the fuel and oxygen sources that are fuel rich, that is, above the combustion stoichiometry for the fuel used.

The fuel mixes with an oxygen source and contacts a catalyst structure that includes at least one metal selected from the Group VIII and/or Group IB metals of the Periodic Table and/or tin to partially oxidize the fuel source, providing more valuable fuels and intermediates, such as, for example, ethylene, propylene, longer chain α-olefins, and syngas.

Significantly, the process of the present invention provides a controllable process for the production of relatively high selectivities of alkenes and syngas by use of an evaporator mixer system. Using this system, the fuel is delivered to the reactor and vaporized, where it is mixed with the oxygen source and contacted with the catalyst. The fuel is preferably delivered using a fuel injector apparatus, such as an automobile gasoline fuel injector. This type of injector typically delivers fuel from pressurized tanks into the reactor. The flow rate typically is controlled by the tank pressure and by the duty cycle (the percentage of time the injector remains open). The duty cycle and the tank pressure determine the fuel flow rates, and the frequency determines how constant the flow rate is, by determining the number of times the injector opens in a second. The higher the frequency, the more continuous the fuel flow. Processes of the invention using this type of fuel injector generally include injectors operated at a frequency of at least about 3 Hertz (Hz). Typically the frequency is no greater than about 10 Hz. Additionally, the duty cycles used in processes of the present invention are typically at least about 1%. Typically duty cycles used are preferably no greater than about 30%.

The evaporator mixer system of the present invention is significant in facilitating the reaction of preferred fuels and, thus, providing the advantageous product selectivities made available by processes of the present invention. The evaporator mixer provides a film of fuel on the sides of the heated reactor. The film is preferably a thin film of at least about monomolecular thickness. Preferably the film thickness is no greater than about 1,000 microns (μm), more preferably no greater than about 500 μm, and most preferably no greater than about 250 μm. Without being held to any particular theory, it is believed that as the film is adjacent to the heated reactor walls, a temperature gradient is created inside the film. This gradient allows the fuel to vaporize at temperatures well below the fuel boiling point and provides a safer reaction, since a fuel source in a vaporized state that is mixed with an oxygen source typically is explosive. For example, the auto-ignition temperature of a normal alkane typically decreases with increasing chain length, but the boiling point typically increases with increasing chain length. For larger hydrocarbons, such as some of the preferred fuels of the present invention, the boiling point can exceed the auto-ignition temperature, resulting in a danger of flaming and explosion. Using the evaporator mixer system of the present invention, however, the film of liquid fuel adjacent to the heated reactor walls is formed, and mixed with the oxygen source and vaporized, prior to contacting the catalyst, providing vaporized fuel that is typically below the auto-ignition temperature of the larger hydrocarbons. Thus, these heavier fuels are able safely to mix with oxygen, and to react, at temperatures below the auto-ignition temperature of the fuel.

Figure 1A:
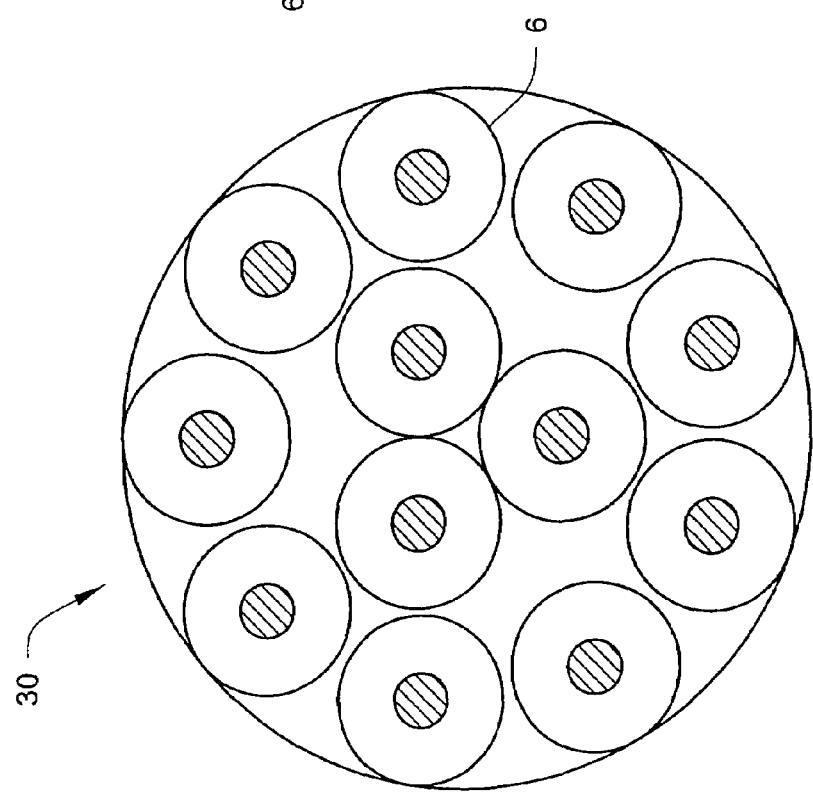

A preferred injector sprays the fuel in a conical shape, creating a film of the fuel on pre-heated reactor walls. It is believed that this film of fuel is significant in the present processes by providing a temperature gradient. Therefore, any fuel delivery method that is able to provide this film on the reactor walls may be used in the present invention, for example, an accurate flow pump, such as a syringe pump, with a conical nozzle. Additionally, a vaporization apparatus such as is shown in FIG. 1, may be used. FIG. 1B shows an array of reactors 20. Each reactor includes a separate delivery system for the fuel source 2, which is delivered separately from the oxygen source 4. The walls of the reactor 6 are preheated, and a film of the fuel 8 is created on the reactor walls and vaporized. The vaporized fuel source and oxygen source contact the catalyst 10, and the reaction product is collected at the downstream side of the catalyst 12. A top view of this array 30 is shown in FIG. 1A as a typical manner in which the reactors may be arranged; however, such a vaporization array is not limited to this configuration.

The arrangement of FIG. 1 shows that the fuel delivery method need not necessarily be a fuel injector. Any fuel delivery system may be used, provided it is able to supply the film of fuel on the heated reactor walls in the manner described herein for preferred embodiments of the invention. Additionally, FIG. 1 shows a possible apparatus for a staged injector system that includes multiple reactor surfaces. Such a staged reactor system may be advantageously used in the present invention, for example, for large scale production of the products (e.g., alkenes and syngas). A staged reactor system, for example, allows the delivery of a greater quantity of fuel per reactor surface area as is available in the reactor apparatus described in the following examples.

Preferred flow rates are a factor in providing preferred time periods during which the vaporized fuel and oxygen mixture contacts the catalyst. Preferred contact time of the fuel source and oxygen source with the catalyst is at least about 5 milliseconds. Preferably the vaporized fuel and oxygen source mixture contacts the catalyst for a period of no greater than about 25 milliseconds.

To provide these preferred contact times for the production of the products, such as syngas, the production of ethylene and propylene, and the production of α-olefins, the mixture of the fuel source and the source of oxygen contacts the catalyst at a flow rate of at least about 0.5 standard liters per minute (SLPM). Additionally, the fuel source and oxygen mixture preferably contacts the catalyst at a flow rate of no greater than about 20 SLPM.

More preferably, for the production of syngas, the flow rate of the fuel and oxygen source is at least about 2 SLPM, and most preferably at least about 3 SLPM. Furthermore, for syngas production, the flow rate of the fuel and oxygen source is more preferably no greater than about 10 SLPM and most preferably no greater than about 8 SLPM.

More preferably, for the production of ethylene and propylene, the flow rate of the fuel and oxygen source is at least about 4 SLPM, and most preferably at least about 6 SLPM.

More preferably, for the production of α-olefins, the flow rate of the fuel and oxygen source is at least about 2 SLPM, and most preferably at least about 3 SLPM. Furthermore, for α-olefin production, the flow rate of the fuel and oxygen source is more preferably no greater than about 12 SLPM and most preferably no greater than about 10 SLPM.

Any reactor capable of containing a catalyst of the invention, capable of accepting a fuel flow from a fuel injector, and capable of containing the reactants at preferred temperatures is appropriate for use in the present invention. A preferred reactor material is quartz; however any material, such as ceramic, is appropriate for use in a reactor, provided it can withstand the reaction temperatures. The reactor can be of any shape, provided contact time with the catalyst is maintained. A tube shaped reactor is preferred. Additionally, a tube shaped reactor can be of any length desired, provided catalyst contact time is maintained. Preferred tube shaped reactors are preferably at least about 45 centimeters (cm) in length, and more preferably at least about 55 cm in length. Preferred reactors are typically no longer than about 80 cm in length. Additionally, the tube reactor can be of any convenient inner diameter, provided catalyst contact time is maintained and the reactor is able to adequately hold the catalyst. Preferred reactors of the present invention have an inner diameter of, typically, at least about 18 millimeters (mm). Typically, the preferred reactors of the present invention have inner diameters of no greater than about 5 cm.

The fuel injector typically provides a conical dispersion of fuel droplets. These droplets have a diameter that is preferably at least about 25 micrometers ($\mu$m), more preferably at least about 50 $\mu$m. Furthermore, the droplet diameters are preferably no greater than about 500 $\mu$m, and more preferably no greater than about 150 $\mu$m. These droplets create a film of liquid fuel on inner walls of the reactor. Without being held to any particular theory, the inventors believe that the film generally tends to absorb heat and vaporize near the wall, where there is generally comparatively little oxygen because the fuel concentration here is comparatively high. Since vaporization and mixing of the fuel with the oxygen source typically occurs substantially simultaneously, the vaporized film near the wall substantially reduces or eliminates regions that contain a fuel mixture that is combustible at a temperature above the auto-ignition temperature.

Reactions at the catalyst according to the processes of the present invention are preferably carried out under autothermal conditions, more preferably under autothermal, nearly adiabatic conditions. "Nearly adiabatic conditions" are defined herein as systems in which the heat loss of the system is negligible. Under autothermal conditions, all the heat required to drive the reactions of the system at the catalyst forward is provided by the exothermic reactions present in the system. That is, the heat produced by the exothermic partial oxidation reaction provides the heat to drive forward the endothermic reactions providing the desired products. Once the catalyst is ignited, the process does not require any further addition of heat. Furthermore, autothermal, nearly adiabatic operation in the present processes is preferred to avoid coke formation.

Liquid fuels are typically preheated prior to contacting the catalyst to provide a vapor. Preferred preheat temperatures of the fuels, vaporized and contacted with the oxygen source substantially simultaneously, of the present invention are typically at least about 25° C., more preferably at least about 50° C., above the boiling point of the fuel source prior to contacting the catalyst. Furthermore, fuel preheat temperatures are typically no greater than about 150° C., more preferably no greater than about 100° C., above the boiling point of the fuel source prior to contacting the catalyst.

Preferred catalysts of the present invention include at least one metal selected from metals defined under the CAS system as Group VIII and Group IB of the Periodic Table. These groups are also known as Groups 8-11 under alternative nomenclature. Group VIII and Group IB include iron, ruthenium, osmium, cobalt, rhodium, iridium, nickel, palladium, platinum, copper, silver and gold. Herein these metals are referred to as Group VIII and Group IB metals. Preferably the catalyst includes at least one Group VIII and Group IB metal disposed on a support. Preferred catalysts also include tin, which is Group IVA of the Periodic Table (also known as Group 14 under alternative nomenclature). More preferably, catalysts of the present invention include at least platinum, rhodium, and combinations thereof. Preferably, the Group VIII and Group IB metals and tin are deposited in an amount of at least about 0.5 weight percent, more preferably at least about 1 weight percent, and even more preferably at least about 3 weight percent, based on total weight of the support and catalyst. Preferably the Group VIII and Group IB metals and tin are deposited in an amount of no greater than about 10 weight percent, more preferably no more than about 8 weight percent, and even more preferably no more than about 6 weight percent, based on total weight of the support and catalyst.

Typically, the metal is deposited from a metal salt solution. Generally, any organic liquid in which the metal salt is soluble may be used to deposit metals onto preferred supports. The metals may also be deposited from aqueous solution using water soluble salts. The metal may also be deposited on the support by, for example, chemical vapor deposition.

Preferred supports of the present invention include a monolithic carrier, that is, a carrier of the type including one or more monolithic bodies having a plurality of finely divided gas flow passages extended therethrough. Such monolithic carrier members are often referred to as "honeycomb" type carriers and are well known in the art. A preferred form of such carrier is made of a refractory, substantially inert, rigid material that is capable of maintaining its shape and a sufficient degree of mechanical strength at temperatures of, for example, about 1500° C. Typically a material is selected for the support that exhibits a low thermal coefficient of expansion, good thermal shock resistance, and low thermal conductivity.

A more preferred support of the present invention includes a ceramic foam monolith such as disclosed in U.S. Pat. No. 4,568,595, which discloses honeycombed ceramic foams with a surface having a ceramic sintered coating closing off the cells, and U.S. Pat. No. 4,253,302, which discloses a foamed ceramic containing platinum/rhodium catalyst as an exhaust gas catalyst. The foam structure is characterized by the number of pores per linear inch (ppi). Preferred ceramic foam monoliths include those with at least about 10 ppi (approximately 394 pores per meter). Preferably monoliths of the present invention include those with no greater than about 100 ppi (approximately 3937 pores per meter). A more preferred ceramic foam monolith includes about 80 ppi (approximately 3110 pores per meter).

Preferred supports further include supports made from metals and metal oxides selected from the group of α-alumina and magnesium aluminum silicate (cordierite). Preferably, the monolith support is washcoated to increase the surface area of the catalyst and to reduce the pore size of the monolith, thereby not only increasing the surface area, but also decreasing the probability that a species will pass through the catalyst without reacting on the surface. The washcoat is typically applied by coating an aqueous solution of, for example γ-alumina on the monolith and allowing the aqueous solvent to evaporate off.

Preferred fuels of the present invention include organic compounds, such as hydrocarbons, of any size, and furthermore, also preferably include mixtures of organic compounds. More preferred organic compounds, however, include at least 6 carbon atoms. Even more preferably, organic compounds of the present invention include at least 10 carbons, and most preferably include at least 16 carbons. While the number of carbons in organic compounds that are useful in the present invention need not be limited, preferred organic compounds include no more than 30 carbon atoms. Particularly preferred fuels of the present invention, however, are liquids that are vaporized and mixed with an oxygen source prior to contact with a catalyst.

Preferred organic compounds useful as a fuel source of the present invention are hydrocarbons. These include branched, straight chain, and cyclic aliphatics that may be either saturated or unsaturated, preferably alkanes, aromatics, and combinations thereof. Further, preferred alkanes of the present invention include linear alkanes (n-alkanes), branched alkanes, cyclic alkanes, and combinations thereof. However, n-alkanes are preferred as reactants for producing products including α-olefins.

Preferred fuels include organic compounds, such as hydrocarbons, of a single size, for example decane and hexadecane. Preferred fuels of the present invention also include mixtures of various sizes of organic compounds, and also include mixtures such as mixtures of alkanes and aromatics. Additionally, the present invention is advantageous in that fuels that contain sulfur may be used as reactants without requiring the sulfur to be removed prior to reaction. Such preferred mixtures of organic compounds advantageously used as fuels in the present invention include, but are not limited to, diesel fuel, low sulfur diesel fuel, biodiesel, JP-8 military fuel, JP-4 military fuel, heavy distillates, kerosene, gasoline, naphtha, plant oils, vegetable oils, and combinations thereof.

The fuel source of the present invention is mixed with an oxygen source prior to contacting a catalyst. The oxygen source may be introduced to the reactor in liquid form or in gaseous form; however a gaseous form is preferred. Preferred oxygen sources include air, oxygen-enriched air, and molecular oxygen. The choice of oxygen source may be selected as appropriate to the application. For instance, for applications such as automotive fuel reforming, air is typically preferred. Also, for large scale operations, air is generally an efficient and economical oxygen source. However, for such applications as olefin production, pure $O_2$ may be preferred. That is, certain preferred processes of the present invention include a source of oxygen that is substantially free of nitrogen. The processes of the present invention are appropriate for a wide variety of oxygen sources.

For preferred processes including air as the oxygen source, nitrogen is present in the air in an atomic ratio of no greater than about 6:1 nitrogen to oxygen. More preferably, nitrogen is present in the air in an atomic ratio of no greater than about 4:1 nitrogen to oxygen. For reactions producing syngas, if air is used as the oxygen source, nitrogen is most preferably present in the air in an atomic ratio of at least about 3.5:1 nitrogen to oxygen. Also, most preferably, if air is used as the oxygen source for syngas production, nitrogen is present in an atomic ratio of no greater than about 4:1 nitrogen to oxygen.

The carbon to oxygen (C/O) atomic ratio of the fuel and oxygen source mixture reacted is significant in determining the reaction products. For example, good selectivities of syngas are typically produced using C/O atomic ratios preferably at least about 0.5, more preferably at least about 0.7. Also, preferred C/O atomic ratios for the production of syngas are preferably no greater than about 1.5, and more preferably no greater than about 1.2. Furthermore, a decrease in the C/O ratio, with the flow rate held constant, typically will cause a decrease in syngas production and an increase in production of the combustion products ($CO_2$ and $H_2O$). Additionally, in combination with the selected flow rate, the C/O atomic ratio of the reactants determines the reaction temperature.

To produce syngas, a preferred C/O atomic ratio is at least about 0.3, a more preferred atomic ratio is at least about 0.5, and even more preferably the atomic ratio is at least about 0.6 C/O. One consideration is, however, that as the C/O ratio approaches the combustion stoichiometry (C/O=0.3) with the flow rate held constant, the reaction temperature increases. Therefore, although the process preferably may be run at a C/O ratio of about 0.3:1 and yield preferred products, there is a danger of flaming or of the reactor exploding. Therefore, more preferably, C/O atomic ratios of the present invention are at least about 0.5 carbon to oxygen. Furthermore, to produce syngas by the processes of the present invention, C/O atomic ratios are preferably no greater than about 2, and more preferably no greater than about 1.

Using these preferred C/O ratios, and under the preferred processes of the present invention, the selectivity of syngas is preferably at least about 60 percent. That is, of the total reaction products, at least about 60 percent of the product is syngas. More preferably syngas is produced at a selectivity of at least about 85 percent. Additionally, the selectivity of syngas under these preferred process conditions is preferably no greater than about 100 percent, and more preferably no greater than about 90 percent.

To produce shorter chain alkenes, for example ethylene and propylene, the C/O atomic ratio used is preferably at least about 0.8, and more preferably is at least about 1. Additionally, to produce alkenes the C/O atomic ratio is preferably no greater than about 5, more preferably no greater than about 2, and even more preferably no greater than about 1.5 carbon to oxygen. Using these preferred C/O ratios and under the preferred conditions of the present invention, ethylene is preferably produced. At these C/O atomic ratios ethylene is preferably produced at a selectivity of at least about 35 percent, and more preferably at least about 50 percent. Furthermore, ethylene is preferably produced by the present processes at a selectivity of no greater than about 100 percent, and more preferably no greater than about 95 percent.

Additionally, under the preferred conditions for production of ethylene, propylene is, preferably, also produced. Furthermore, propylene is preferably produced at a selectivity of at least about 15 percent, and more preferably at least about 20 percent. The selectivity of propylene under these conditions is, preferably, no greater than about 50 percent, and more preferably no greater than about 40 percent.

To produce α-olefins, particularly α-olefins including 4 or more carbon atoms, the fuel source is preferably present in a C/O atomic ratio of at least about 2, and more preferably at least about 2.5 carbon to oxygen. Furthermore, the fuel source is preferably present in a C/O atomic ratio of no greater than about 10, more preferably no greater than about 5, even more preferably no greater than about 4, and most preferably no greater than about 3.5 carbon to oxygen. Using these preferred C/O ratios and under preferred conditions of the present invention, the selectivity of α-olefin reaction products is preferably at least about 20 percent, and more preferably at least about 50 percent. Furthermore, the selectivity of α-olefin products under preferred conditions of the present invention is preferably no greater than about 100 percent, and more preferably no greater than about 95 percent.

Additionally, processes of the present invention may advantageously be reacted without adding water to the reaction. This is advantageous because there is no need for the added step of removing unreacted water from the products. Furthermore, by not adding water to the reactions, the reactions typically yield a higher selectivity of desired products and greater product output. Therefore, water is preferably not present. The present processes, however, are also suitable for reaction in the presence of water, preferably added in the form of water vapor. For reactions in which water is present, water is preferably present in a ratio of no greater than about 20, water molecule to carbon atom. More preferably, if water is present, the water is present in a ratio of no greater than about 10, water molecule to carbon atom.

EXAMPLES

Objects and advantages of this invention are further illustrated by the following examples, but the particular materials and amounts thereof recited in these examples, as well as other conditions and details, should not be construed to unduly limit this invention.

The reforming by partial oxidation, according to the processes of the present invention, of two of the major components of diesel fuel: n-decane and n-hexadecane is described here. These fuels can be quantified by detailed mass balances to determine conversions and selectivities to various products. Additionally, the partial oxidation of a low sulfur grade of diesel fuel is described. Since the low sulfur diesel fuel is a mixture of hydrocarbons, quantitative analysis of reactants and products of the partial oxidation of the diesel fuel is more complicated, as is specification of the carbon to oxygen (C/O) stoichiometry.

Catalyst

The catalyst substrate used in the present examples was an 18 millimeter (mm) diameter and 10 mm length a-$Al_2O_3$ ceramic foam monolith with 80 pores per linear inch (ppi) (Vesuvius Hi-Tech Ceramics, Alfred Station, N.Y.).

In the following examples, four different types of catalysts were used. The first type of catalyst was a washcoated rhodium catalyst, the second type was a nonwashcoated rhodium catalyst, the third type was a nonwashcoated platinum-rhodium catalyst, and the fourth type was a nonwashcoated platinum catalyst.

The washcoated rhodium catalyst was prepared by first washcoating the monolith with approximately 5 wt %, based on total weight of the monolith, of γ-$Al_2O_3$ to roughen and increase the catalyst surface area (Bodke, A. S., Bharadwaj, S. S., Schmidt, L. D., *Journal of Catalysis*, 179:138 (1998)). The washcoated monolith was then coated with about 4 wt % rhodium, based on total weight of the monolith and catalyst, by immersing it in approximately 3 milliliters (ml) Stock #12633 aqueous $Rh(NO_3)_3$ solution (Alfa Aesar, Ward Hill, Mass.) and calcining it in an oven for approximately 6 hours at approximately 600 degrees Celsius (° C.).

The nonwashcoated rhodium catalyst was prepared by coating the monolith with about 4 wt % rhodium, based on total weight of the monolith and catalyst. The monolith was immersed in approximately 3 milliliters (ml) Stock #12633 aqueous $Rh(NO_3)_3$ solution (Alfa Aesar, Ward Hill, Mass.) and calcined in an oven for approximately 6 hours at approximately 600 degrees Celsius (° C.).

The nonwashcoated platinum-rhodium catalyst was prepared by coating the monolith with about 4 wt % platinum-rhodium (in the ratio of 10 to 1 by weight), based on total weight of the monolith and catalyst. The monolith was immersed in approximately 3 milliliters (ml) of solution containing Stock #12633 aqueous $Rh(NO_3)_3$ solution (Alfa Aesar, Ward Hill, Mass.) and Stock #17822BA aqueous $H_2PtCl_6$ solution (Sigma-Aldrich Chemical Company, Milwaukee, Wis.). The coated monolith was then cacined in an oven for approximately 2 hours at approximately 600 degrees Celsius (° C.).

The nonwashcoated platinum catalyst was prepared by coating the monolith with about 4 wt % platinum, based on total weight of the monolith and catalyst. The monolith was immersed in approximately 3 milliliters (ml) of solution containing Stock #17822BA aqueous $H_2PtCl_6$ solution (Sigma-Aldrich Chemical Company, Milwaukee, Wis.). The coated monolith was then calcined in an oven for approximately 2 hours at approximately 600 degrees Celsius (° C.).

A total of 250 runs were performed using fifteen catalysts prepared as indicated above. Each catalyst operated for approximately 10 hours, with no catalyst deactivation observed at exit temperatures maintained below about 1100° C.

Evaporator Mixer System

The evaporator mixer system used in the present invention and as described herein, provides substantial prevention of flaming of the fuel upon vaporization and mixing with an oxygen source. The evaporator mixer as described herein includes a fuel injector and reactor. However, an evaporator mixer system of the present invention is not limited to the embodiment described herein. Without being held to any particular theory, it is believed that any apparatus that is capable of delivering a liquid film onto the reactor walls provides an appropriate evaporator mixer system of the present invention.

Fuel Injector for Fuel Vaporization and Mixing

The auto-ignition temperature of normal alkanes decreases as the chain length increases and is as low as about 200° C. for alkanes above n-decane. Since the boiling point increases with chain length, the boiling point typically exceeds the auto-ignition temperature for alkanes higher than n-decane. During vaporization and mixing of fuel with oxygen, the interface between the vaporized fuel and oxygen necessarily produces mixtures varying from pure fuel to pure oxygen. Since the temperature of vaporization may be above the auto-ignition temperature for certain higher alkanes, such mixture could spontaneously ignite, producing flames and explosions. Diesel fuel typically contains mostly linear alkanes ranging from $C_8$ to $C_{20}$, most of which have higher boiling point than auto-ignition temperatures.

In the present examples an automotive gasoline fuel injector (Delphi Automotive Company, Troy, Mich.) was attached to the top of a quartz reactor tube and used as the fuel delivery method to facilitate vaporization and mixing of reactants before contacting the catalyst. Pressurized fuel at 5 pounds per squared inch read from a pressure gauge (psig) was fed into the injector, which was computer operated at frequency of about 3 Hertz (Hz) and at duty cycles, the percentage of time that the injector remains open, from about 1% to about 15%. Thus, the liquid flow rate delivered by the injector was controlled accurately by the pressure in the fuel supply tank and by the duty cycle. The fuel delivery rate was calibrated at different pressures, frequencies, and duty cycles prior to conducting the following examples and was found accurate to within ±2%.

Reactor

Figure 2A:
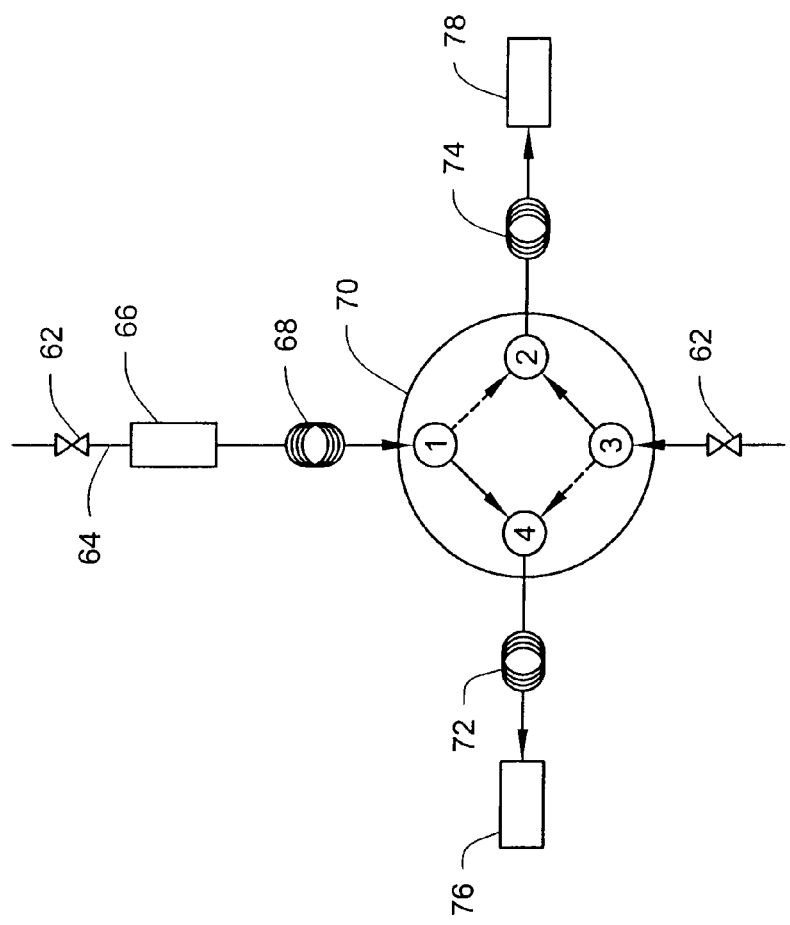
FIGS. 2A and 2B. Schematic of a typical reactor including an evaporator mixer system (A) and gas chromatograph (B).

The evaporator mixer system used in the following examples is shown in FIG. 2(a). The reactor 40 consisted of a quartz tube with a 19 mm inner diameter and was 55 centimeters (cm) in length. The fuel 42 was delivered to the reactor 40 from the top, using a fuel injector 44 as described above, creating a film of fuel 45 on the reactor walls. The oxygen source used, air 46, was separately delivered to the reactor from the top. The reactor walls were pre-heated to a temperature of between about 250 degrees Centigrade (° C.) and 400° C., depending on the fuel boiling temperature. The pre-heat temperature was at least about 50° C. and no greater than about 150° C. higher than the boiling point of the fuel used. Heating tape 48 and insulation 50 was provided around the reactor to prevent dissipation of heat. Blank monoliths 52 were provided on either side of the catalyst 54 to act as a heat shield. The back face temperature of the catalyst 54 was measured with a thermocouple 56 and the reaction products 58 were recovered at the downstream side of the catalyst.

Oxygen Source

Air, rather than pure $O_2$, was used in the following examples to reduce the possibility of flames and explosions.

Reactor Temperatures

A significant variable in selecting an appropriate fuel flow rate and C/O ratio of the reactants to produce the desired produce is the reactor temperature. Furthermore, processes of the present invention are preferably carried out under auto-thermal, nearly adiabatic operation, because with dilution in a furnace the temperatures will never be high enough to avoid coke formation, and high temperatures in the reactor before the catalyst typically will cause homogeneous combustion and soot formation. For the size of the monolith used in the present examples (approximately 1.8 centimeters (cm) diameter and 1 cm long) and with heat shields and insulation around the catalyst tube, the measured temperature at the exit of the catalyst was typically found to be within 100° C. of the calculated adiabatic temperature.

Furthermore, for producing syngas from methane via partial oxidation, the temperature within the catalyst can be as much as 300° C. higher than the exit temperature (the temperature at the back face of the catalyst) (Kein, E. J., Tummala, S., Schmidt, L. D., *Stud. Surf. Sci. Catal.*, 136:245 (2001); while for ethane, oxidative dehydrogenation to ethylene the temperature is seldom more than 100° C. above the exit temperature (Henning, D. A., Schmidt, L. D., *Chem. Eng. Sci.*, 57(14):2615 (2002)). Since the present examples provide both syngas and olefins, it is believed that the temperature within the catalyst is, therefore, between 100° C. and 300° C. above the measured exit temperatures.

The fuel sources used in the present examples were typically heated to a temperature of at least about 250° C., and typically no greater than about 400° C., depending on the boiling point of the fuel reacted, prior to contacting the catalyst.

Carbon to Oxygen Ratios

The present examples were carried out using C/O ratios in the combined fuel and oxygen source from the lowest C/O being 0.5 to the highest C/O ratio being 3.0 without any evident deterioration in performance over at least several hours. The lower limit, 0.5, was set by the maximum temperatures that the catalyst was believed to be able to withstand without metal loss. Therefore C/O ratios of less than 0.5 were seldom used. The upper C/O limit was selected according to the conversion of reactants to products. The fuel flow rate and the C/O ratio used determine the reactor temperature, and low reactor temperatures it was found result in low conversion. Therefore, although the process performs at C/O ratios higher than about 3, high C/O ratio processes that produced an alkane conversion of less than 50% were not preferred.

It was surprisingly found that carbon formation before and within the catalyst did not substantially shut down the present processes. It was anticipated that the catalyst would frequently become quenched as graphite is thermodynamically stable for the feed compounds used at all temperatures if C/O ratios are greater than 1, and graphite is predicted at equilibrium at lower temperatures, such as about 600° C., for C/O ratios less than 1. It was occasionally found that the catalyst extinguished because of carbon formation, but this was found typically to be due to inadequate heating of the fuel, allowing liquid fuels to contact the catalyst.

There was some carbon observed on the used catalysts in all the following examples. As anticipated, carbon tended to form more around the edges of the catalyst where the temperature was lower. If coking was suspected, the catalyst was regenerated by operating at lower C/O ratios to remove it. Also, by switching from a reacting mixture to pure air an exotherm in temperature of up to 100° C. could be measured.

Without being held to any particular theory, it is believed that the substantial absence of coking in the present processes is caused by the water formed in the reaction and that water typically removes carbon by steam reforming to CO. Oxygen is present in the first half, which is considered the upstream portion, of the catalyst, so any carbon on the surface is typically oxidized off. The presence of monolayer amounts of carbon in the second half, or downstream portion, of the catalyst, in the presence of a relatively poor concentration of oxygen, is believed to somewhat deactivate the rhodium surfaces. This slight deactivation is believed to prevent further side reactions, such as reaction of olefins to form acetylenes and aromatics, that typically leads to additional coke formation.

Diesel Fuels

The liquid hydrocarbons used as a fuel source were high purity HPLC grade (99+%), purchased from Sigma-Aldrich Chemical Company (Milwaukee, Wis.), except for the diesel fuel, which was a California phase 2 low sulfur diesel, purchased from British Petroleum (BP, Los Angeles, Calif.). An analysis of this diesel showed that it consisted of 90.2% alkanes, 2.1% alkenes and 7.9% aromatics, with less than 10 parts per million (ppm) sulfur, and an average molecular formula of $C_{14.5}H_{31}$. The reactor was operated at atmospheric pressure.

The characterization of products and conversion of a multicomponent logistic fuel, such as a diesel fuel, is more complex than with a single fuel component. In addition to these complexities, there are other issues in reforming that arise because of the nature of diesel fuel.

First, the stoichiometry (the C/O ratio) is not precisely described for a mixture with varying number of carbon atoms and variable C/H ratios. Thus, in the present examples the C/O ratios of the diesel fuel reactants were described by assuming an average molecule containing 14.5 carbon atoms and 31 hydrogen atoms. This was believed to be a substantially accurate approximation for the diesel fuel reacted because it was well characterized. However, other logistics fuels typically may have variable compositions. Since $H_2$ and CO are typically produced with maximum selectivity for C/O of approximately 1, it is believed that this maximum could be broadened and lowered or shifted with a fuel mixture because some components are above and below the optimum stoichiometry for $H_2$ production.

Second, the reactivities of different molecules may be quite different. Linear, branched, and cyclic alkanes typically do not react identically. Aromatic and polyaromatic molecules typically have different reactivities than aliphatics. Differences in reactivities may also be observed between pyrolysis and in oxidation reactions, and between homogeneous and surface processes. It is believed that these reactivities are in all probability correlated with autoignition temperatures, which may vary by as much as 100° C. between fuel components of fuels such as logistics fuels.

Furthermore, oxidation reactions may have different order of reactivities than pyrolysis reactions. Oxidation reactions typically depend on reactions with $O_2$, OH, O, $H_2O$, and related alkyl species where, unlike in pyrolysis reactions, reactivities do not correlate with bond strength but are more sensitive to molecular geometry and electronic structure.

Even less is known regarding the relative surface reactivities of these components and their variation with size and structure. For instance, adsorption and decomposition is believed to be quite different on a rhodium washcoated catalyst than, for example, on an alumina catalyst without rhodium because the rhodium has a much greater capability to adsorb $O_2$, which promotes surface oxidation channels. On alumina, decomposition might therefore be expected to have a greater tendency to form coke.

Additionally, a fundamental possible complication with partial oxidation of fuel mixtures is that reactivities are not simply an average over all reactant molecules, as the most reactive component in a mixture generally will consume all $O_2$ very quickly. This typically will leave pyrolysis in an $O_2$ free environment as the only reaction channel for less reactive components. For example, according to this analysis, if aromatics are less reactive than aliphatics, the aromatics can only undergo pyrolysis reactions. This would generally not be preferred because aromatics, being hydrogen deficient compared to aliphatics, must inevitably pyrolyze to coke and soot.

Fuel vaporization is also different for mixtures because boiling points vary. Diesel fuel typically boils from 100° C. to 300° C., so fractional distillation will occur if evaporation is slow. The highest boiling fraction is believed to be highest in polyaromatics, which is believed to have the greatest tendency to decompose to coke before evaporating. Without being held to any particular theory, it is believed that the evaporator mixing system used in the present processes produces a substantially rapid vaporization and, thus, avoids excessive distillation to leave a residue. The relative amounts of evaporation in the drops from the fuel injector and at the wall are expected, however, to vary with the drop size, air and fuel temperature, and with the distance between injector and wall. Furthermore parameters such as surface temperature, heat flux to the surface, fuel delivery rate, and mixing concentration profiles are also expected to have influences on diesel fuel vaporization and mixing.

Despite these difficulties in production and quantitative analysis of olefins and syngas from logistics fuels, such as diesel fuel, the present processes have successfully demonstrated the partial oxidation of low sulfur diesel to produce a hydrogen-rich mixture. The present examples demonstrate that it is possible to oxidize higher alkanes to syngas and to olefins by partial oxidation in air at contact times of 5 to 25 milliseconds. The process is substantially robust in that the catalyst can be operated successfully over a wide range of C/O ratios as long as the liquid fuel is substantially simultaneously vaporized and mixed with air prior to contacting the catalyst, and the catalyst is kept sufficiently hot.

Furthermore, the present processes are substantially insensitive to catalyst form and loading, and it is believed that the present processes may be "tuned" beyond the results of the present examples by changing the catalyst material or form. Thus, even higher yields of syngas or of light or large olefins are believed to be obtainable by modifications apparent to one of skill in the art.

The diesel fuel used in the following examples was a high grade of diesel fuel that contains low sulfur (10 ppm), aromatics (8%), and olefins (2%) compared to a conventional diesel fuel. These components is believed could cause problems, such as catalyst deactivation caused by sulfur poisoning, in high concentrations.

It is possible to operate the reactor in the presence of water, either by adding it with a separate fuel injector or with an emulsion. This enables the water gas shift in the short contact time reactor to produce high $H_2$/CO ratios, which are required in fuel cell applications.

Product Analysis

Figure 2B:
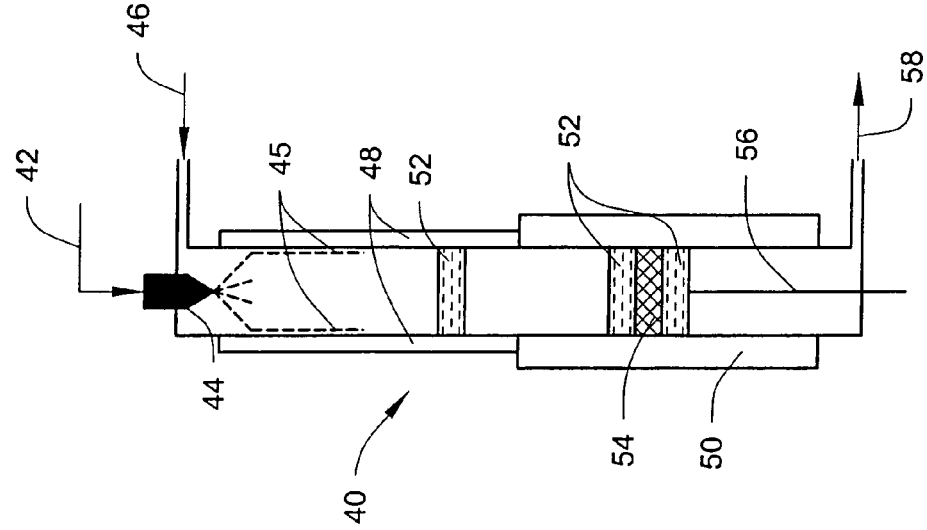
Figure 3A:
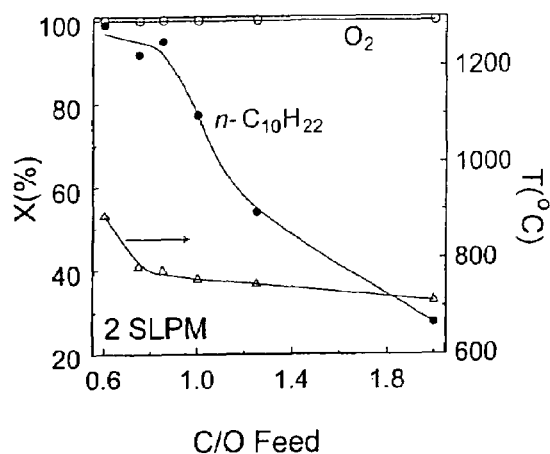
FIG. 3A-3D. Graphs indicating the effect of n-decane/oxygen feed ratio on the fuel and oxygen conversions and the catalyst back face temperature at 2, 4, 6, and 8 standard liters per minute (Figs. A, B, C, and D, respectively) using a washcoated rhodium coated alumina ceramic foam monolith catalyst.
Figure 3B:
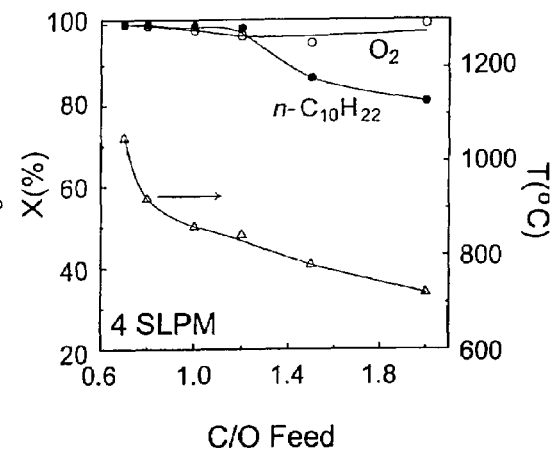
Figure 3C:
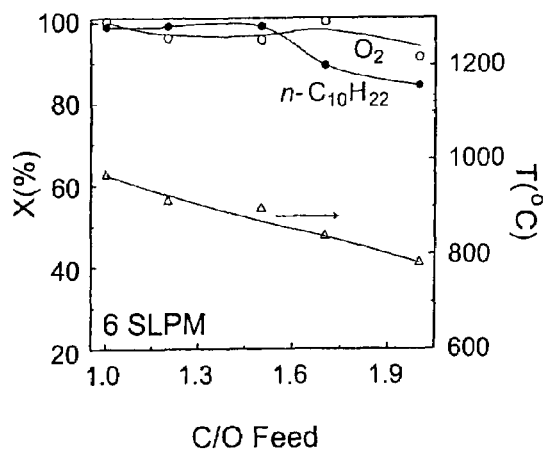
Figure 3D:
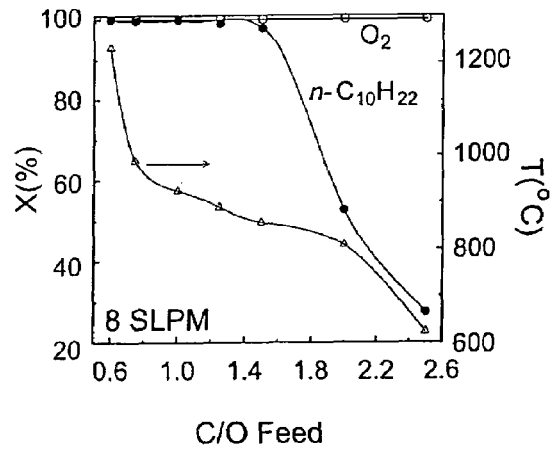
Figure 4A:
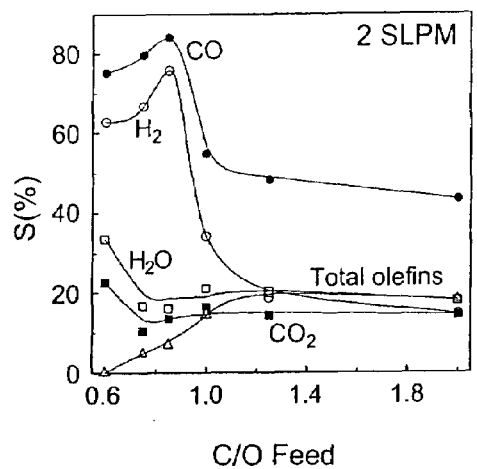
FIG. 4A-4D. Graphs indicating the effect of n-decane/oxygen feed ratio on the product selectivities at 2, 4, 6, and 8 standard liters per minute (Figs. A, B, C, and D, respectively) using a washcoated rhodium coated alumina ceramic foam monolith catalyst.
Figure 4B:
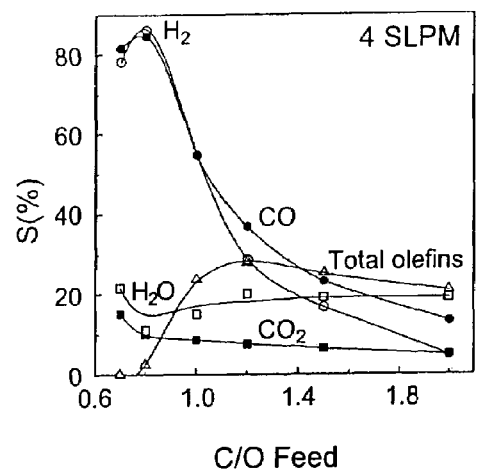
Figure 4C:
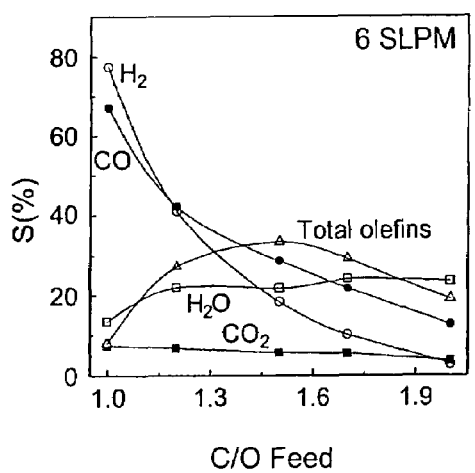
Figure 4D:
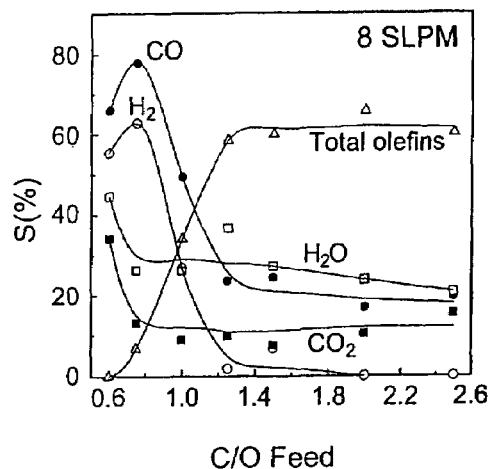
Figure 5A:
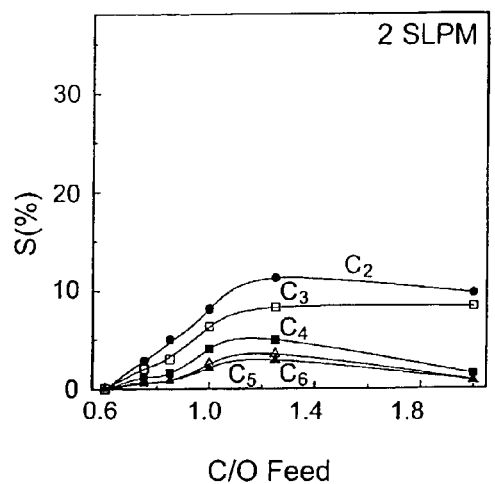
FIG. 5A-5D. Graphs indicating the effect of n-decane/oxygen feed ratio on ethylene ($C_2$), propylene ($C_3$), 1-butene ($C_4$), 1-pentene ($C_5$), and 1-hexene ($C_6$) at 2, 4, 6, and 8 standard liters per minute (Figs. A, B, C, and D, respectively) using a washcoated rhodium coated alumina ceramic foam monolith catalyst.
Figure 5B:
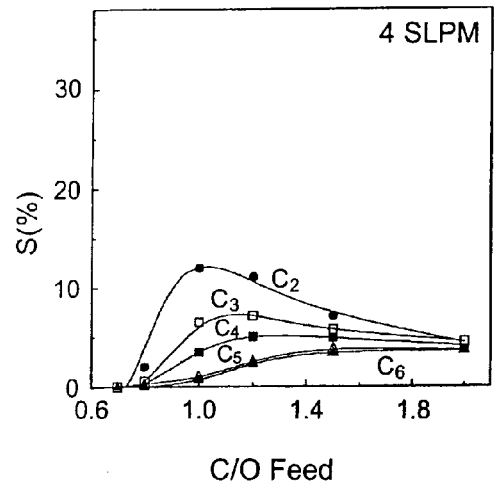
Figure 5C:
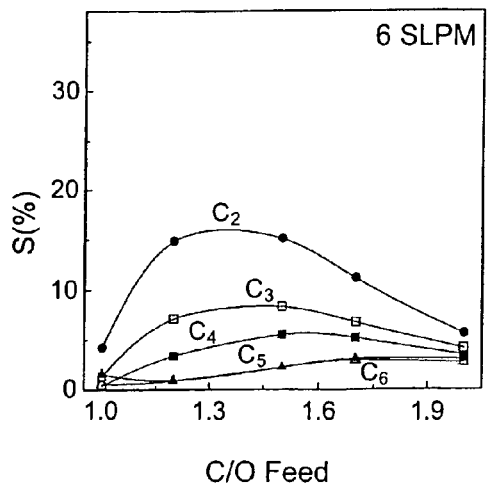
Figure 5D:
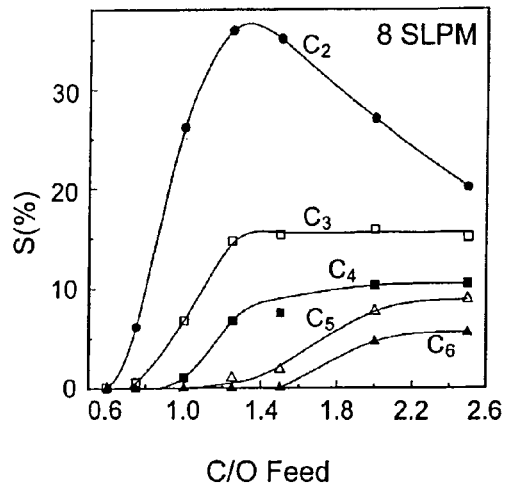

The product stream typically consists of a mixture of permanent gases, liquids (after cooling), and un-reacted fuel. Analyzing such a mixture using a gas chromatograph or mass spectrometer can be challenging because columns that can separate liquids typically cannot separate permanent gases. Therefore a dual column system, including a pre-column, was adapted for use in the present examples (Allen K. Vickers; Daron Decker; Jason Ellis, "PLOT column configurations for the gas chromatic analysis of ozone precursors" J&W Scientific publication, August, 1998) and installed in a 5890 Series II Hewlett-Packard Gas Chromatograph (GC), as shown in FIG. 2(b) (Hewlett Packard, Palo Alto, Calif.). Helium 62 was used as the carrier gas. The product samples 64 were injected into a DB-1 capillary pre-column 68 (15 meters (m) in length, 0.32 mm Inner Diameter (ID), 0.25 µm dimethylsiloxane (DMSO) film at the injection port 66. The permanent gases typically traveled faster through the pre-column than did the hydrocarbons. The 4-way switching valve 70 was initially set at position 1, where the permanent gases were sent to a Heyesep D (Alltech, model 100/120, Deerfield, Ill.) packed column 72 (9 m in length, 2.2 mm ID). This column separated the permanent gases at room temperature. After the permanent gases left the pre-column, the valve 70 was switched to position 2, sending the hydrocarbons to a DB-1 (J&W Scientific, model DB-1, Folsom, Calif.) capillary column 74 (60 m in length, 0.32 mm ID, 0.25 µm DMSO film). The permanent gases were analyzed using a TCD (thermal conductivity detector) 76 and the hydrocarbons were analyzed using an FID (flame ionization detector) 78 which were both supplied with the Gas Chromatograph (Hewlett-Packard, Palo Alto, Calif.). Nitrogen was used as the calibration standard, carbon and hydrogen balances typically closed within ±8% error. All products were incinerated in a fume hood and vented.

This GC system was insufficient to analyze the larger hydrocarbon products (greater than (>) $C_{10}$) that resulted from the partial oxidation of n-hexadecane because the large number of GC peaks made the analysis intractable. Therefore, a GC mass spectrometer (GC-MS) (Hewlett-Packard, Palo Alto, Calif.) was used to analyze heavier products in a separate analysis. The hydrocarbon products were condensed in acetone and analyzed. In all cases the results showed that most of the hydrocarbon products, approximately 99%, were α-olefins. The GC-MS also quantified alkanes and olefin fractions.

Examples 1-23 n-decane

Example 1

A washcoated rhodium coated alumina ceramic foam monolith catalyst, prepared as described above, was placed in a reactor configured as described above. The reactor was maintained at a pressure of approximately 1 atmosphere (atm) throughout the process. Two blank 80 ppi ceramic foam monoliths (Vesuvius Hi-Tech Ceramics, Alfred Station, N.Y.) were placed immediately upstream (the region of the reactor between where the fuel and oxygen enter the reactor and the catalyst) and downstream from the catalyst. The blank monoliths acted as axial heat shields and were used to promote additional radial mixing. All three monoliths were wrapped with FIBERFRAX (Unifrax Corporation, PS3338, Niagara Falls, N.Y.) alumina-silica paper to avoid bypassing of gasses between the monoliths and the reactor wall. A chromel-alumel k-type thermocouple (Omega Engineering, Inc., Stamford, Conn.) was placed between the backside of the upstream blank monolith and the catalyst to measure the "back face" temperature. Alumina-silica insulation (Unifrax Corporation, Niagara Falls, N.Y.) was placed around the reactor to reduce radial heat loss.

Oxygen and nitrogen (the oxygen source) at the atomic ratio of approximately 3.76 N/O were initially heated and admitted to the reactor to heat the catalyst and walls of the reactor. The flow rates of the oxygen source, high purity $N_2$ and $O_2$, entering the reactor from high-pressure cylinders were adjusted to approximately 2 standard liters per minute (SLPM) using mass flow controllers that were accurate to ±0.05 SLPM. The oxygen source released heat to the catalyst, heating it to a temperature of about 200° C., measured at the back face of the catalyst using a thermocouple. The catalyst ignited within about 15 seconds.

Liquid n-decane was then introduced with the fuel injector into the pre-heated section of the reactor. The fuel vaporized and mixed with the oxygen source at a temperature of about 250° C. and at a C/O ratio of about 0.8 (atomic ratio of 0.8:1 carbon to oxygen). The fuel and oxygen mixture contacted the catalyst at a contact time of approximately 24 milliseconds (ms). The reaction was allowed to run for about 30 minutes, at which time the backface temperature of the catalyst stabilized at approximately 770° C., heated as a result of the exothermicity of the reaction.

A sample of the reaction product was then removed from the reactor using a 500 microliter syringe and analyzed as described above. The oxygen source was shut off, then the fuel source was shut off. The oxygen source was then allowed to flow again for approximately one minute to burn off any potential amount of coke that may have formed on the catalyst surface during the reaction. The oxygen source was then shut off.

The reaction products obtained were $H_2$ (76%), CO (84%), $H_2O$ (16%), $CO_2$ (14%), ethylene (5%), and α-olefins (7%), the values representing hydrogen atom or carbon atom selectivity.

Example 2

The process of example 1 was followed, except that the flow rate of the oxygen source and the fuel source was 4 SLPM, the catalyst contact time was 12 ms, and the catalyst back face temperature was about 920° C. The reaction products obtained were $H_2$ (86%), CO (84%), $H_2O$ (11%), $CO_2$ (10%), ethylene (2%), and α-olefins (3%).

Example 3

The process of example 1 was followed, except that the flow rate of the oxygen source and the fuel source was 6 SLPM, the catalyst contact time was 8 ms, and the catalyst back face temperature was about 970° C. The reaction products obtained were $H_2$ (77%), CO (67%), $H_2O$ (13%), $CO_2$ (7%), ethylene (4%), and α-olefins (8%).

Example 4

The process of example 1 was followed, except that the flow rate of the oxygen source and the fuel source was 8 SLPM, the catalyst contact time was 6 ms, and the catalyst back face temperature was about 990° C. The reaction products obtained were $H_2$ (63%), CO (78%), $H_2O$ (26%), $CO_2$ (13%), ethylene (6%), and α-olefins (7%).

Example 5

The process of example 1 was followed, except that the atomic carbon to oxygen ratio used was about 1.2 C/O. The catalyst back face temperature for this reaction was about 750° C. The reaction products obtained were $H_2$ (19%), CO (48%), $H_2O$ (20%), $CO_2$ (14%), ethylene (11%), and α-olefins (20%).

Example 6

The process of example 5 was followed, except that the flow rate of the oxygen source and the fuel source was 4 SLPM, the catalyst contact time was 12 ms, and the catalyst back face temperature was about 840° C. The reaction products obtained were $H_2$ (29%), CO (37%), $H_2O$ (20%), $CO_2$ (8%), ethylene (11%), and α-olefins (28%).

Example 7

The process of example 5 was followed, except that the flow rate of the oxygen source and the fuel source was 6 SLPM, the catalyst contact time was 8 ms, and the catalyst back face temperature was about 910° C. The reaction products obtained were $H_2$ (41%), CO (42%), $H_2O$ (22%), $CO_2$ (7%), ethylene (15%), and α-olefins (27%).

Example 8

The process of example 5 was followed, except that the flow rate of the oxygen source and the fuel source was 8

SLPM, the catalyst contact time was 6 ms, and the catalyst back face temperature was about 890° C. The reaction products obtained were $H_2$ (2%), CO (24%), $H_2O$ (37%), $CO_2$ (10%), ethylene (36%), and α-olefins (58%).

Example 9

The process of example 1 was followed, except that the atomic carbon to oxygen ratio used was about 2:1 C/O. The catalyst back face temperature for this reaction was about 710° C. The reaction products obtained were $H_2$ (15%), CO (43%), $H_2O$ (18%), $CO_2$ (14%), ethylene (10%), and α-olefins (18%).

Example 10

The process of example 9 was followed, except that the flow rate of the oxygen source and the fuel source was 4 SLPM, the catalyst contact time was 12 ms, and the catalyst back face temperature was about 720° C. The reaction products obtained were $H_2$ (5%), CO (13%), $H_2O$ (19%), $CO_2$ (5%), ethylene (4%), and α-olefins (21%).

Example 11

The process of example 9 was followed, except that the flow rate of the oxygen source and the fuel source was 6 SLPM, the catalyst contact time was 8 ms, and the catalyst back face temperature was about 780° C. The reaction products obtained were $H_2$ (3%), CO (13%), $H_2O$ (24%), $CO_2$ (4%), ethylene (6%), and α-olefins (19%).

Example 12

The process of example 9 was followed, except that the flow rate of the oxygen source and the fuel source was 8 SLPM, the catalyst contact time was 6 ms, and the catalyst back face temperature was about 810° C. The reaction products obtained were $H_2$ (0%), CO (17%), $H_2O$ (24%), $CO_2$ (10%), ethylene (27%), and α-olefins (66%).

FIG. 3 shows the conversion of n-decane and oxygen and the catalyst back face temperature at the total vapor flow rates studied. The oxygen conversion observed was greater than 90% for all ratios and flow rates. The n-decane conversion observed was greater than 99% for C/O ratios less than 1.2 at high flow rates, such as 6 and 8 SLPM, particularly 8 SLPM, and it decreased slightly as the feed became more fuel rich for all flow rates. The catalyst back face temperature increased with increasing flow rate it is believed because at higher flow rates, the rate of heat generation increased, causing the reactor to operate closer to adiabatic. The catalyst back face temperature decreased as the fuel conversion decreased.

FIG. 4 shows the selectivities to synthesis gas (CO and $H_2$), combustion products ($CO_2$ and $H_2O$), and olefins for these examples. The highest yield observed in these examples for both $H_2$ and CO for all flow rates occurred at C/O=0.8, a ratio slightly lower than syngas stoichiometry. The shift in the C/O ratio at which high syngas yield occurs is believed to be attributed to the presence of homogeneous chemistry, which typically causes the gas phase stoichiometry to differ from the surface stoichiometry. Selectivity for $H_2$ of 86% and for CO of 84% occurred at 4 SLPM and a C/O atomic ratio of about 0.8. The combustion products increased as the feed ratio approached the combustion stoichiometry. The syngas selectivity dropped and the olefin selectivity increased as the feed became more fuel rich (C/O greater than 1). The olefin products consisted of almost exclusively α-olefins ranging from ethylene to 1-hexene, and selectivity of 63% occurred at 8 SLPM. Without being held to any particular theory, it is believed that the C/O ratio used is a factor in providing longer chain α-olefins versus ethylene and/or propylene.

FIG. 5 shows the selectivities to olefin products in detail. Ethylene had the highest selectivity observed in these examples with 36% at 1.2<C/O<1.5 and 8 SLPM. The ethylene selectivity dropped at leaner or richer ratios. At higher C/O ratios, the yield to higher α-olefins increased and at lower ratios the yield to syngas increased. Selectivity for propylene of 16%, 1-butene of 10%, 1-pentene of 9%, and 1-hexene of 6% was obtained at C/O=2.5 and 8 SLPM.

In all the foregoing examples, the total selectivity to all alkane products was less than 8% (not shown). The alkane selectivities increased with the C/O feed ratio and became approximately 0% at C/O less than 1. The alkane products were mostly methane (greater than 95%) and small amounts of ethane and propane. In some instances traces of butane were observed.

Examples 13-23

Example 13

The process of example 1 was followed except that the catalyst used was a non washcoated rhodium coated alumina ceramic foam monolith, the flow rate of the oxygen source and the fuel source was 8 SLPM, the catalyst contact time was 8 ms, and the catalyst back face temperature was about 1300° C. The reaction products obtained were $H_2$ (71%), CO (62%), $H_2O$ (23%), $CO_2$ (10%), ethylene (4%), and α-olefins (24%).

Example 14

The process of example 13 was followed, except that the atomic carbon to oxygen ratio used was about 1.2 and the catalyst back face temperature was about 1050° C. The reaction products obtained were $H_2$ (27%), CO (30%), $H_2O$ (26%), $CO_2$ (8%), ethylene (36%), and α-olefins (51%).

Example 15

The process of example 13 was followed, except that the atomic carbon to oxygen ratio used was about 2:1 and the catalyst back face temperature was about 900° C. The reaction products obtained were $H_2$ (6%), CO (14%), $H_2O$ (23%), $CO_2$ (5%), ethylene (24%), and α-olefins (75%).

Figure 6A:
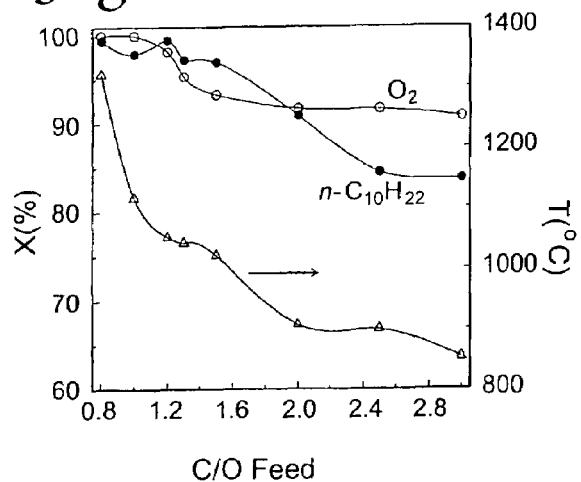
FIG. 6A-6C. Graphs indicating the effect of n-decane/oxygen feed ratio on the fuel and oxygen conversions, the back face temperature, and product selectivities (Figs. A, B, and C, respectively) including ethylene ($C_2$), propylene ($C_3$), and 1-butene ($C_4$) selectivities at 8 standard liters per minute using a nonwashcoated rhodium coated alumina ceramic foam monolith catalyst.

FIG. 6(a) shows the conversion of n-decane and oxygen and the catalyst back face temperature at a total vapor flow rate of 8 SLPM and several C/O ratios. The oxygen conversion was greater than 90% for all ratios. The n-decane conversion was greater than 98% for C/O ratios less than 1.2, and it decreased slightly as the feed became more fuel rich. The catalyst back face temperature decreased as the fuel conversion decreased.

Figure 6B:
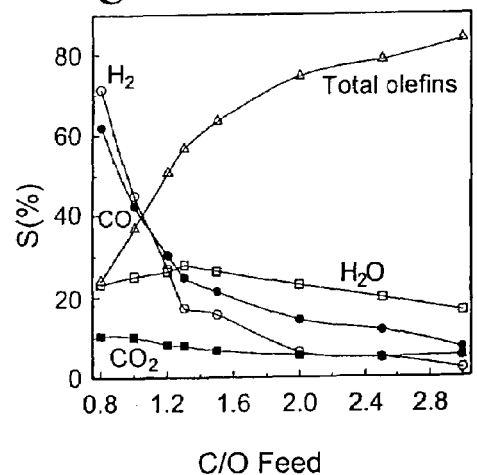

FIG. 6(b) shows the selectivities to synthesis gas (CO and $H_2$), combustion products ($CO_2$ and $H_2O$), and olefins for these examples. The highest yield observed in these examples in both $H_2$ and CO for all flow rates occurred at C/O=0.8, a ratio slightly lower than syngas stoichiometry. The shift in the C/O ratio at which high syngas yield occurs is believed to be attributed to the presence of homogeneous chemistry, which typically causes the gas phase stoichiometry to differ from the surface stoichiometry. Selectivity for $H_2$ was 71% and for CO was 62% at a C/O atomic ratio of about 0.8. The combustion products increased as the feed ratio approached the combustion stoichiometry. The syngas selectivity dropped and the olefin selectivity increased as the feed became more fuel rich (C/O greater than 1). The olefin products consisted of almost exclusively α-olefins, ranging from ethylene to 1-hexene, and selectivity of 84% occurred at a C/O atomic ratio of about 3.0. Without being held to any particular theory, it is believed that the C/O ratio used is a factor in providing longer chain α-olefins versus ethylene and/or propylene.

Figure 6C:
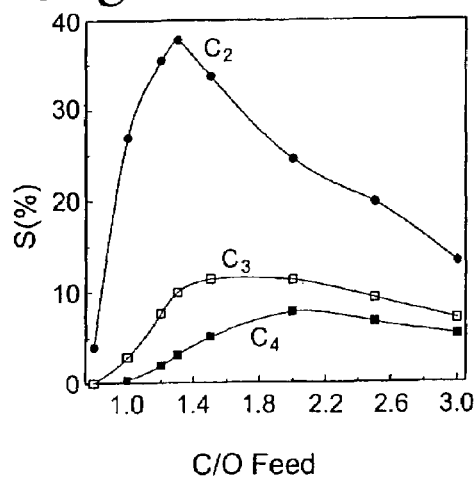

FIG. 6(c) shows the selectivities to olefin products in detail. Ethylene had a selectivity of 38% at a C/O ratio of 1.3. The ethylene selectivity dropped at leaner or richer ratios. At higher C/O ratios, the yield to higher α-olefins increased and at lower ratios the yield to syngas increased. Selectivity of propylene was 11% at a C/O of 1.5, and selectivity of 1-butene was 8% at a C/O of 2.

Example 16

The process of example 1 was followed, except that the catalyst used was a platinum-rhodium (at the ratio of 10 to 1 by weight) coated alumina ceramic foam monolith (not washcoated), and the catalyst back face temperature was about 900° C. The reaction products obtained were $H_2$ (6%), CO (36%), $H_2O$ (49%), $CO_2$ (10%), ethylene (30%), and α-olefins (44%).

Example 17

The process of example 16 was followed, except that the atomic carbon to oxygen ratio used was about 1.2, and the catalyst back face temperature was about 750° C. The reaction products obtained were $H_2$ (0%), CO (15%), $H_2O$ (44%), $CO_2$ (10%), ethylene (15%), and α-olefins (72%).

Example 18

The process of example 16 was followed, except that the atomic carbon to oxygen ratio used was about 2:1, and the catalyst back face temperature was about 690° C. The reaction products obtained were $H_2$ (0%), CO (10%), $H_2O$ (30%), $CO_2$ (6%), ethylene (14%), and α-olefins (80%).

Example 19

The process of example 16 was followed, except that the atomic carbon to oxygen ratio used was about 0.9 C/O, the flow rate of the oxygen source and the fuel source was 4 SLPM, the catalyst contact time was 12 ms, and the catalyst back face temperature was about 980° C. The reaction products obtained were $H_2$ (19%), CO (41%), $H_2O$ (41%), $CO_2$ (9%), ethylene (28%), and α-olefins (41%).

Example 20

The process of example 19 was followed, except that the atomic carbon to oxygen ratio used was about 1.2 and the catalyst back face temperature was about 860° C. The reaction products obtained were $H_2$ (10%), CO (26%), $H_2O$ (36%), $CO_2$ (6%), ethylene (27%), and α-olefins (60%).

Example 21

The process of example 19 was followed, except that the atomic carbon to oxygen ratio used was about 2:1 C/O, and the catalyst back face temperature was about 690° C. The reaction products obtained were $H_2$ (0%), CO (10%), $H_2O$ (29%), $CO_2$ (6%), ethylene (14%), and α-olefins (80%).

Figure 7A:
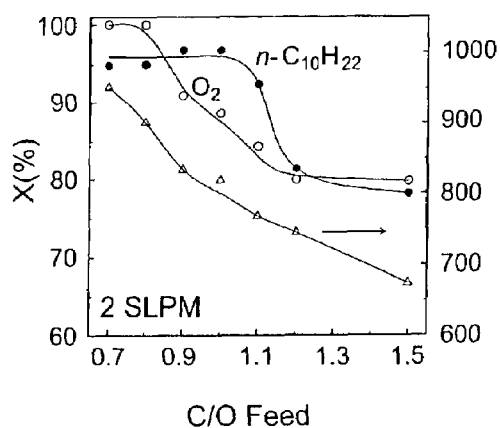
FIG. 7A-7D. Graphs indicating the effect of n-decane/oxygen feed ratio on the fuel and oxygen conversions, the back face temperature, and product selectivites to synthesis gas, combustion products, and total olefins at 2 standard liters per minute (Figs. A and C, respectively) and 4 standard liters per minute (Figs. B and D, respectively) using a nonwashcoated platinum-rhodium (10:1 ratio by weight) coated alumina ceramic foam monolith catalyst.
Figure 7B:
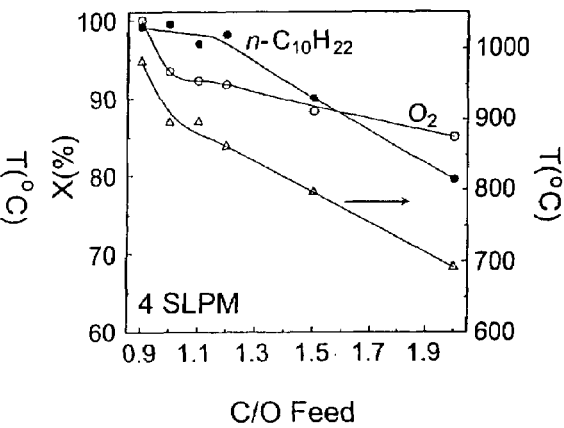

FIGS. 7(a) and (b) show the conversion of n-decane and oxygen and the catalyst back face temperature at the total vapor flow rates studied. The oxygen conversion observed was greater than 80% for all ratios and flow rates. The n-decane conversion observed was greater than 93% for C/O ratios less than 1.2 at all flow rates, and it decreased slightly as the feed became more fuel rich for all flow rates. The catalyst back face temperature increased with increasing flow rate it is believed because at higher flow rates, the rate of heat generation increased, causing the reactor to operate closer to adiabatic. The catalyst back face temperature decreased as the fuel conversion decreased.

Figure 7C:
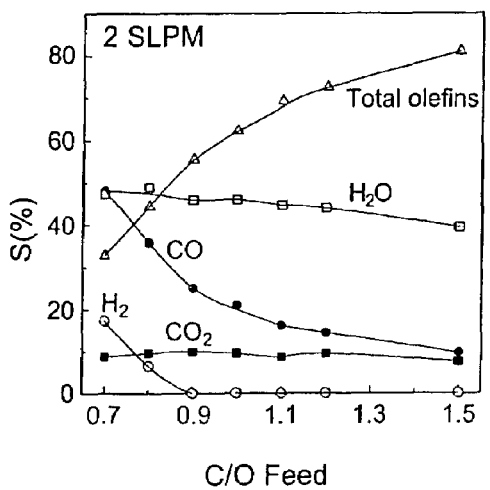
Figure 7D:
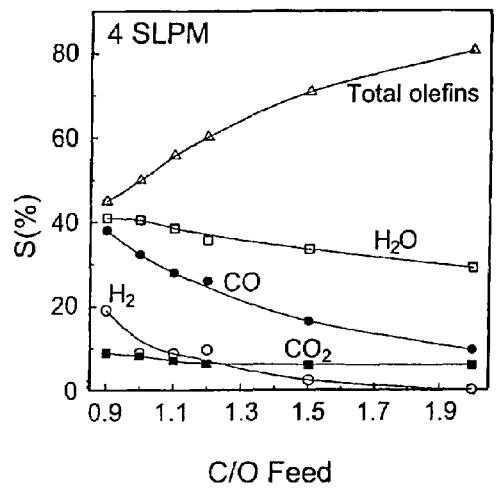

FIGS. 7(c) and (d) show the selectivities to synthesis gas (CO and $H_2$), combustion products ($CO_2$ and $H_2O$), and olefins for these examples. The highest yield observed in these examples in both $H_2$ and CO for 2 SLPM occurred at C/O=0.7, and for 4 SLPM occurred at C/O=0.9, ratios slightly lower than syngas stoichiometry. The shift in the C/O ratio at which high syngas yield occurs is believed to be attributed to the presence of homogeneous chemistry, which typically causes the gas phase stoichiometry to differ from the surface stoichiometry. Selectivity for $H_2$ was 19% and for CO was 41% at 4 SLPM and a C/O atomic ratio of about 0.9. The combustion products increased as the feed ratio approached the combustion stoichiometry. The syngas selectivity dropped and the olefin selectivity increased as the feed became more fuel rich (C/O greater than 1). The olefin products consisted of almost exclusively α-olefins ranging from ethylene to 1-hexene, and selectivity of 81% occurred at both 2 and 4 SLPM. Without being held to any particular theory, it is believed that the C/O ratio used is a factor in providing longer chain α-olefins versus ethylene and/or propylene.

Figure 8A:
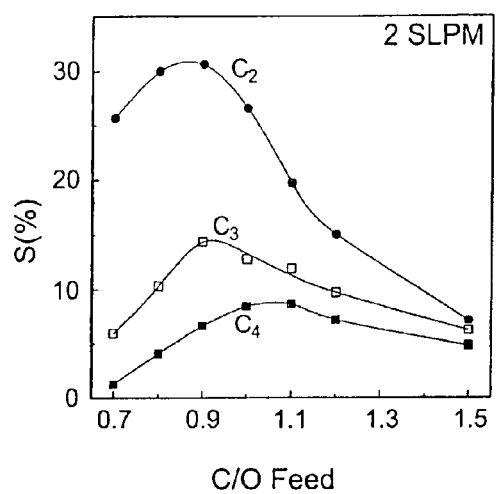
FIG. 8A and 8B. Graphs indicating the effect of n-decane/oxygen feed ratio on the ethylene, propylene, and 1-butene selectivities at 2 and 4 standard liters per minute (Figs. A and B, respectively) using a nonwashcoated platinum-rhodium (10:1 ratio by weight) coated alumina ceramic foam monolith catalyst.
Figure 8B:
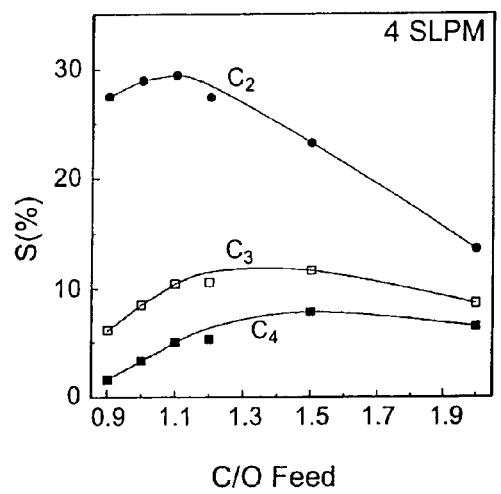

FIG. 8 shows the selectivities to olefin products in detail. Ethylene had a selectivity of 31% at 0.8<C/O<1.0 and 2 SLPM. The ethylene selectivity dropped at leaner or richer ratios. At higher C/O ratios, the yield to higher α-olefins increased and at lower ratios the yield to syngas increased. Selectivities for propylene of 14% and 1-butene of 9% were obtained at C/O=0.9 and 2 SLPM.

Example 22

The process of example 1 was followed, except that the catalyst used was a platinum coated alumina ceramic foam monolith (not washcoated), and the catalyst back face temperature was about 850° C. The reaction products obtained were $H_2$ (0%), CO (16%), $H_2O$ (55%), $CO_2$ (13%), ethylene (13%), and α-olefins (68%).

Example 23

The process of example 22 was followed, except that the atomic carbon to oxygen ratio used was about 1.2 and the catalyst back face temperature was about 790° C. The reaction products obtained were $H_2$ (0%), CO (11%), $H_2O$ (49%), $CO_2$ (7%), ethylene (7%), and α-olefins (81%).

Figure 9A:
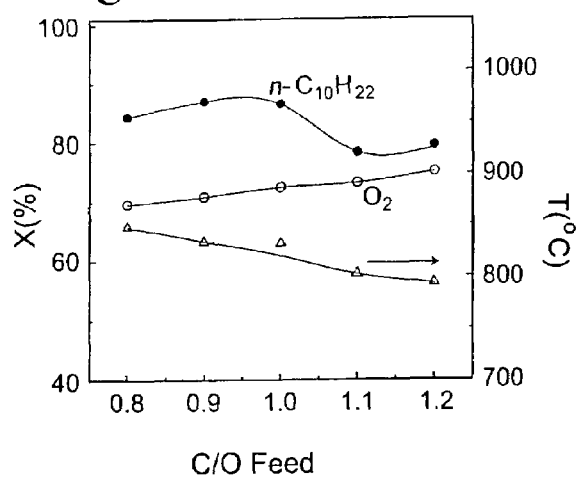
FIG. 9A-9C. Graphs indicating the effect of n-decane/oxygen feed ratio on the fuel and oxygen conversions, the back face temperature, and product selectivities including ethylene, propylene, and 1-butene selectivities (Figs. A, B, and C, respectively) at 2 standard liters per minute using a nonwashcoated platinum coated alumina ceramic foam monolith catalyst.

FIG. 9(a) shows the conversion of n-decane and oxygen and the catalyst back face temperature at a total vapor flow rate of 2 SLPM and several C/O ratios. The oxygen conversion observed was between 70% and 75% for all ratios. The n-decane conversion observed was between 80% and 85% for all ratios. The catalyst back face temperature decreased as the fuel conversion decreased.

Figure 9B:
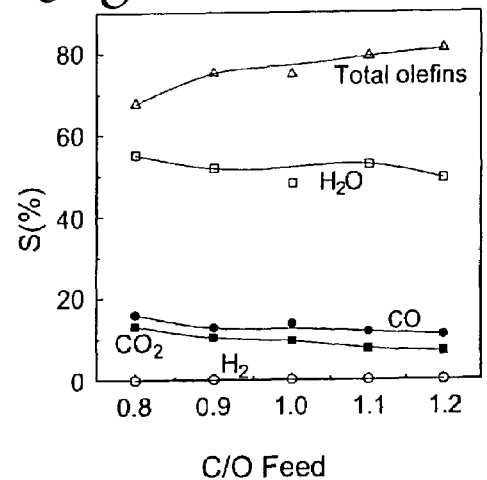

FIG. 9(b) shows the selectivities to synthesis gas (CO and $H_2$), combustion products ($CO_2$ and $H_2O$), and olefins for these examples. The yield of $H_2$ was 0% at all ratios, and that of CO was 16% at C/O=0.8. The combustion products increased slightly as the feed ratio approached the combustion stoichiometry. The olefin products consisted of almost exclusively α-olefins ranging from ethylene to 1-hexene, and a selectivity of 81% occurred at a C/O atomic ratio of about 1.2.

Figure 9C:
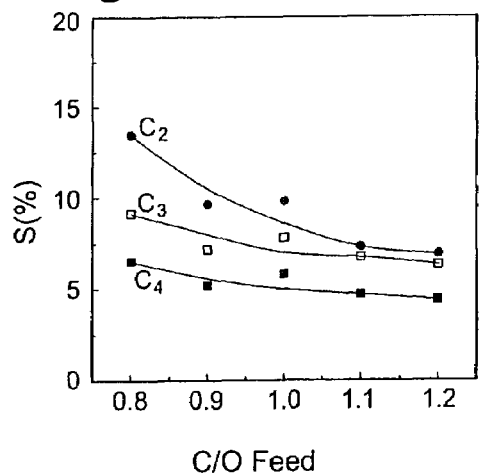
Figure 10A:
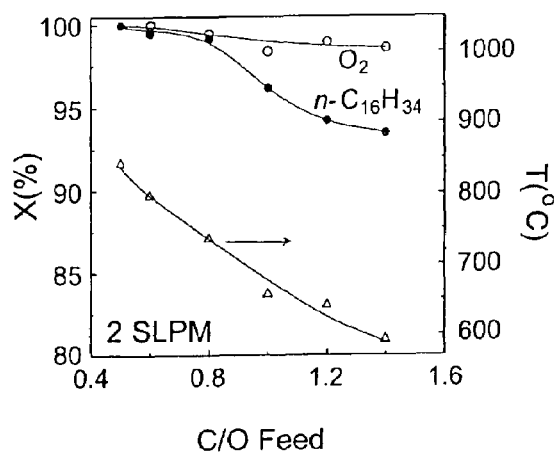
FIG. 10A-10D. Graphs indicating the effect of n-hexadecane/oxygen feed ratio on the fuel and oxygen conversions and the catalyst back face temperature at 2, 4, 6, and 8 standard liters per minute (Figs. A, B, C, and D, respectively) using a washcoated rhodium coated alumina ceramic foam monolith catalyst.
Figure 10B:
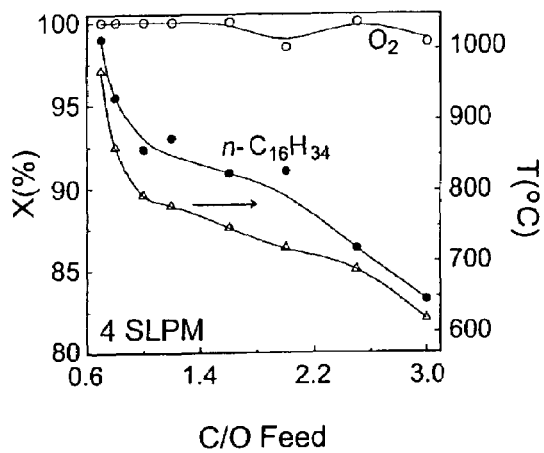
Figure 10C:
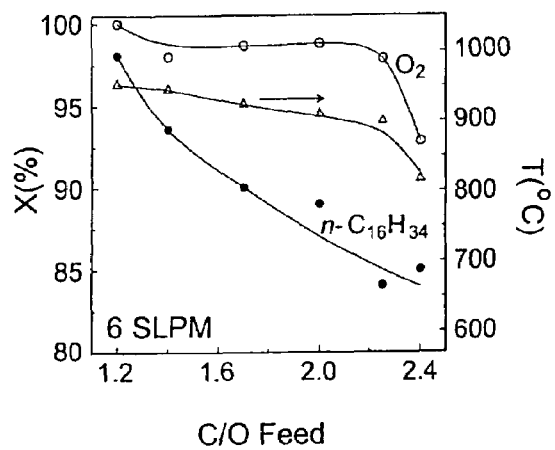
Figure 10D:
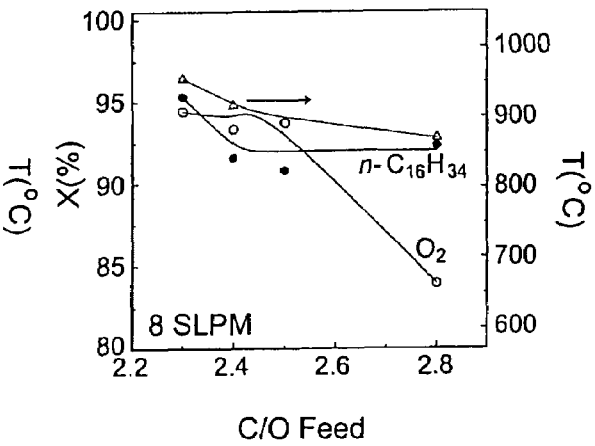
Figure 11A:
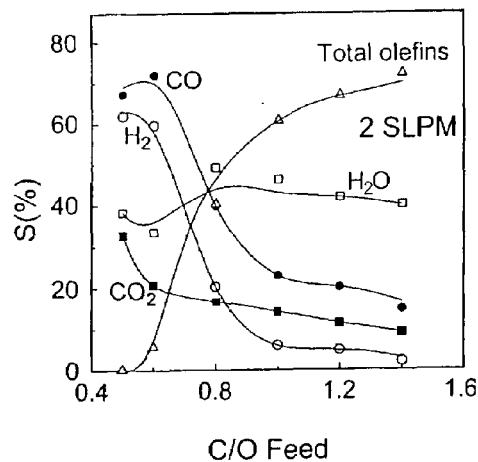
FIG. 11A-11D. Graphs indicating the effect of n-hexadecane/oxygen feed ratio on the product selectivities at 2, 4, 6, and 8 standard liters per minute (Figs. A, B, C, and D, respectively) using a washcoated rhodium coated alumina ceramic foam monolith catalyst.
Figure 11B:
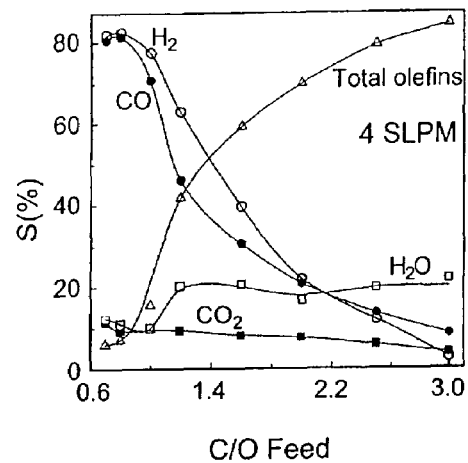
Figure 11C:
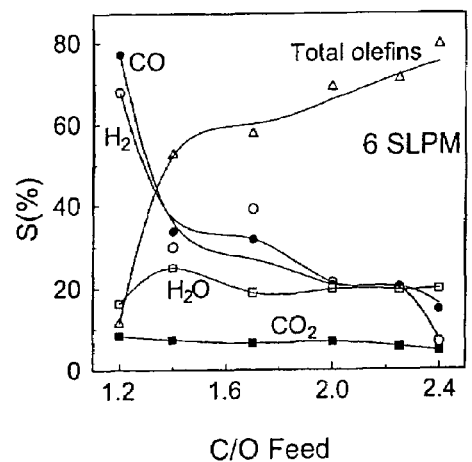
Figure 11D:
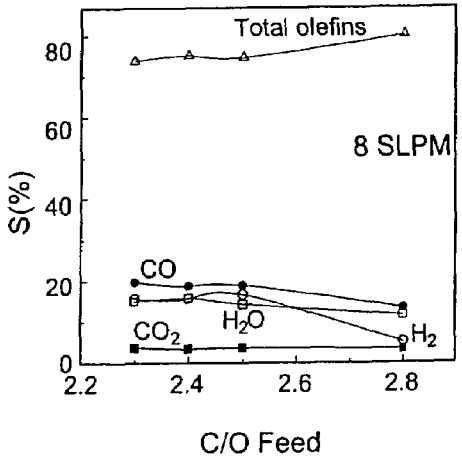
Figure 12A:
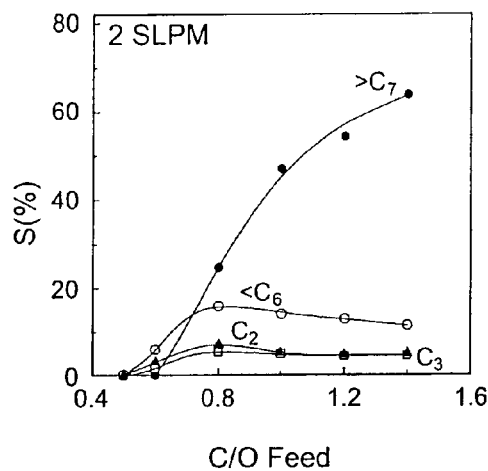
FIG. 12A-12D. Graphs indicating the effect of n-hexadecane/oxygen feed ratio on the ethylene, propylene, and α-olefin selectivities at 2, 4, 6, and 8 standard liters per minute (Figs. A, B, C, and D, respectively) using a washcoated rhodium coated alumina ceramic foam monolith catalyst.
Figure 12B:
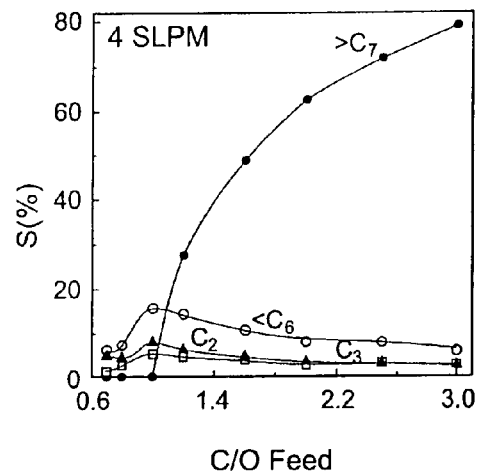
Figure 12C:
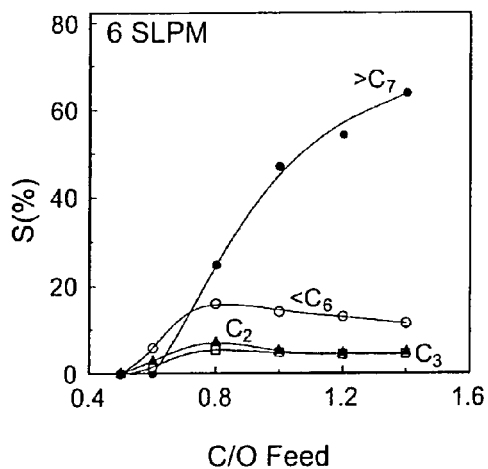
Figure 12D:
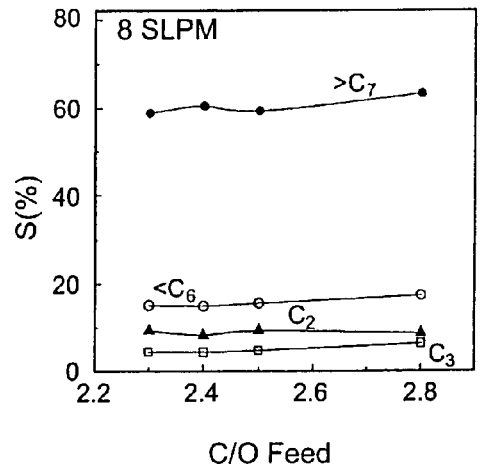
Figure 14A:
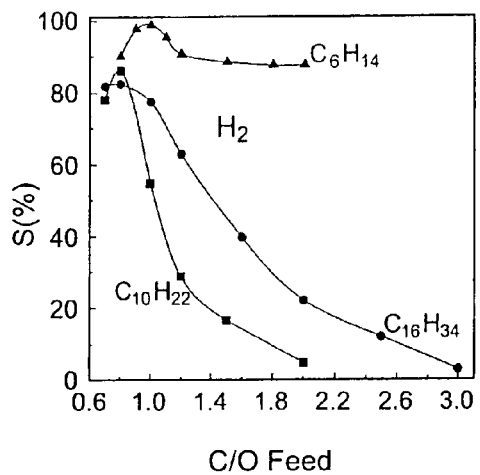
FIG. 14A-14D. Product distribution from n-hexane (2.5 standard liters per minute), n-decane (4 standard liters per minute), and n-hexadecane (4 standard liters per minute) produced by methods known in the art.
Figure 14B:
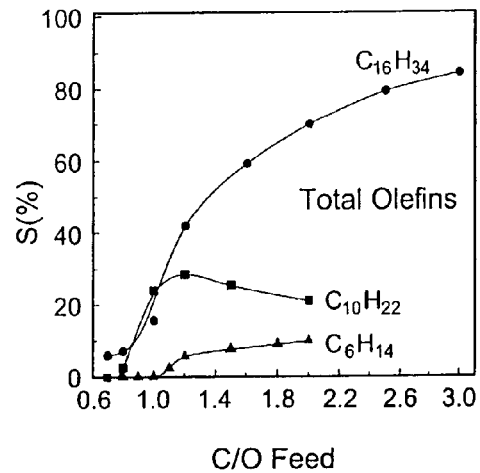
Figure 14C:
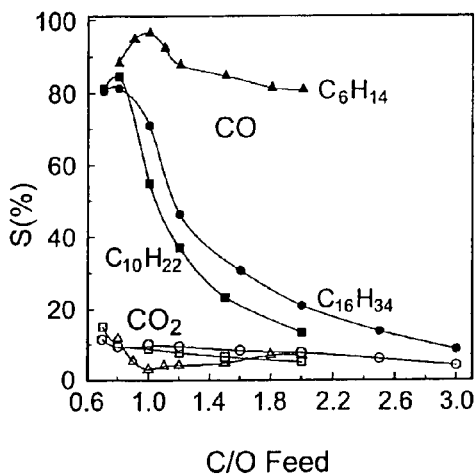
Figure 14D:
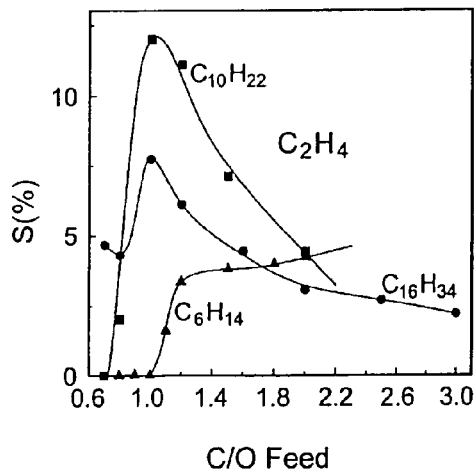

FIG. 9(c) shows the selectivities to olefin products in detail. Ethylene had the highest observed selectivity in these examples, with 13% at a C/O ratio of 0.8. The ethylene selectivity dropped at richer ratios. At all C/O ratios, the yield to higher α-olefins was high. Selectivity for propylene of 9% and selectivity for 1-butene of 7% occurred at a C/O of 0.8.

Examples 24-28 n-hexadecane

Example 24

The process of example 1 was followed, except that n-hexadecane was the fuel source fed to the reactor using the fuel injector, the n-hexadecane was heated to a temperature of 400° C. and mixed with the oxygen source in the heated section of the reactor. The catalyst back face temperature was about 740° C. The reaction products obtained were $H_2$ (21%), CO (40%), $H_2O$ (49%), $CO_2$ (17%), ethylene (7%), and α-olefins (40%).

Example 25

The process of example 24 was followed, except that the flow rate of the oxygen source and the fuel source was 4 SLPM, the catalyst contact time was 12 ms, and the catalyst back face temperature was about 860° C. The reaction products obtained were $H_2$ (82%), CO (81%), $H_2O$ (11%), $CO_2$ (9%), ethylene (4%), and α-olefins (7%).

Example 26

The process of example 1 was followed, except that the atomic carbon to oxygen ratio used was about 2.4 C/O, the flow rate of the oxygen source and the fuel source was about 4 SLPM, and the catalyst contact time was about 12 ms. The catalyst back face temperature for this reaction was about 690° C. The reaction products obtained were $H_2$ (12%), CO (14%), $H_2O$ (20%), $CO_2$ (6%), ethylene (3%), and α-olefins (79%).

Example 27

The process of example 26 was followed, except that the flow rate of the oxygen source and the fuel source was 6 SLPM, the catalyst contact time was 8 ms, and the catalyst back face temperature was about 820° C. The reaction products obtained were $H_2$ (6%), CO (14%), $H_2O$ (20%), $CO_2$ (4%), ethylene (9%), and α-olefins (79%).

Example 28

The process of example 26 was followed, except that the flow rate of the oxygen source and the fuel source was 8 SLPM, the catalyst contact time was 6 ms, and the catalyst back face temperature was about 920° C. The reaction products obtained were $H_2$ (16%), CO (19%), $H_2O$ (16%), $CO_2$ (3%), ethylene (8%), and α-olefins (75%).

Certain reactions were not run for various reasons. For example, at high flow rates (6 and 8 SLPM) at a C/O ratio of 0.8, it was believed the catalyst back face temperature would be high enough to damage the rhodium surface of the catalyst. Also, at low flow rates (2 SLPM) and a C/O ratio of 2.4, it was believed the catalyst back face temperature would be low enough that the reaction could have been extinguished.

FIG. 10 shows that the fuel conversion observed was greater than 95% and the oxygen conversion was 100% at C/O ratio less than 0.8 for all flow rates. The oxygen breakthrough, the amount of unreacted oxygen, increased as the flow rate increased. The catalyst back face temperature followed the same trend as the fuel conversion, decreasing as the C/O feed ratio increased. As the flow rate increased, the range of C/O studied became narrower because lower C/O ratios generally resulted in higher catalyst temperatures, and to prevent rhodium sublimation from the catalyst, the maximum catalyst temperature should not exceed about 1200° C. (Tamman, G., Mansuri, Q. A., *Z. Anorg. Allg. Chem.*, 126:119 (1923).

FIG. 11 shows that syngas selectivities of 82% to $H_2$ and 81% to CO were achieved at C/O=0.8 and 4 SLPM. As the feed became more fuel rich, the syngas selectivity dropped and the olefins selectivity increased. The maximum olefin selectivity observed reached 84% at C/O=3 and a flow rate of 4 SLPM.

FIG. 12 shows the olefins produced in detail. Ethylene and propylene showed the highest selectivities in these examples for olefins with six or less carbon atoms. The selectivities were 8% to ethylene and 5% to propylene at C/O=1 and 8 SLPM. Olefins with six or more carbon atoms had a combined selectivity of 78% at C/O=2 and 4 SLPM. An analysis by GC mass spectrometer, as described above, showed that the large olefin products consisted of α-olefins ranging from $1-C_8H_{16}$ to $1-C_{16}H_{32}$. Total internal olefins were less than 0.5%, and branched alkanes were less than 1%. Trends in the selectivities to alkanes (not shown) were similar to those observed with n-decane.

Examples 29-30

Low Sulfur Diesel Fuel

Example 29

The process of example 1 was followed, except that low sulfur diesel fuel was the fuel source fed to the reactor using the fuel injector, diesel fuel was heated to a temperature of about 350° C. and mixed with the oxygen source in the heated reactor section. The C/O ratio used was 0.35. The reaction ignited when the back face temperature of the catalyst reached approximately 260° C. and the temperature proceeded to rise quickly over approximately 1 minute, reaching an equilibrium temperature after approximately 10 minutes. The catalyst back face temperature was about 1070° C. The reaction products obtained were $H_2$ (68%), CO (82%), $H_2O$ (27%), $CO_2$ (13%), ethylene (2%), and α-olefins (2%).

Example 30

The process of example 29 was followed, except that the C/O ratio used was about 2, and the catalyst back face temperature was about 740° C. The reaction products obtained were $H_2$ (13%), CO (24%), $H_2O$ (27%), $CO_2$ (14%), ethylene (13%), and α-olefins (55%).

The runs with low sulfur diesel were done only at 2 SLPM, as higher flow rates gave back face temperatures in excess of 1100° C. at C/O=1, which can cause chemical and physical changes to the rhodium disposed on the catalyst. As with n-decane and n-hexadecane, the fuel was vaporized in the reactor between 300 and 350° C. and no flames were observed in the reaction chamber at C/O less than 0.35. Flames were observed at C/O=0.3, which was expected with this fuel. Flaming may be expected to occur at different C/O ratios for different types of fuels used. The combustion ratio for this fuel, which was estimated to be $C_{14.5}H_{31}$, is 0.33, consistent with the examples.

Analysis of the lower molecular weight products, less than $C_6$, indicated that for all examples using low sulfur diesel fuel, at least 98% of the reactant material has been converted to products with 6 or fewer carbons for all C/O ratios. The dominant products at C/O ratios near 1 were typically CO and $H_2$, with small amounts of ethylene and $CO_2$.

The product trends, shown in FIG. 13, are similar to those observed for n-decane and n-hexadecane. The back face temperature of the catalyst was typically higher at lower C/O ratios, and this corresponded to higher $H_2$ production. Similarly, higher C/O ratios resulted in the production of more ethylene and propylene. The greatest amount of $H_2$ production observed was achieved at C/O=0.35, although this is expected to vary depending on the diesel fuel used, as different diesel fuels include varying carbon-hydrogen compositions.

Quantification of Diesel Reforming

As diesel fuel is a mixture, with separation of the reactants and products and calibration of GC responses difficult or impossible, analysis of diesel fuel products was more difficult than the analysis of single-molecule products. To estimate the conversion of diesel, it was assumed that all molecules greater than $C_8$ were diesel fuel reactants and that GC responses were the same for all molecules. This clearly gave a lower bound to the conversion, and, further, it is believed that the actual conversion may be higher than shown. In the range of C/O ratios examined, the conversion to products less than $C_8$ is nearly quantitative. Therefore, it is believed that the estimate is fairly accurate.

Selectivities to light olefins and alkanes less than $C_8$ could also be determined relatively accurately because there were no reactant species in the smaller molecular weight range. For products indicating higher molecular weights, where reactants and products overlap, it is believed that most of the species are product olefins by analogy with the products observed from the decane and hexadecane examples.

Products Observed

These results show systematic trends with respect to product selectivities as functions of feed composition and fuel type. For the fuels reacted in the above examples, the selectivity of the products typically changed from predominantly $CO_2$ to CO to small olefins to large olefins as C/O ratio increased. Thus it was shown that the above reactions typically switched from combustion to reforming to dehydrogenation reactions with increasing C/O ratios:

| Products = | $CO_2 + H_2O$ ⇔ $CO + H_2$ ⇔ $C_2H_4$ ⇔ α-olefins. |
|---|---|
| Feed C/O = | <<1 ~1 >1 ~2 |

In previous experiments similar results are observed with $CH_4$ (Hickman, D. A., Schmidt, L. D., *Science,* 259:343 (1993); Otsuka, K., et al., *Stud. Surf. Sci. Catal.,* 61:15 (1991)), $C_2H_3$ to $C_4H_{10}$ alkanes (Otsuka, K., et al., *Stud. Surf. Sci. Catal.,* 61:15 (1991); Huff, M., et al., *Stud. Surf. Sci. Catal.,* 81:315 (1994); Goetsch, D. A., Schmidt, L. D., *Science,* 271:1560 (1996)), and n-hexane, cyclohexane, and isooctane (O'Connor, R. P., Klein, E. J., Schmidt, L. D., *Catalysis Letters,* 70:99 (2000); Dietz, A. G. I., Carlsson, A. F., Schmidt, L. D., *Journal of Catalysis,* 176:459 (1998)).

FIG. 10 provides a comparison of the present results with previous experiments using n-hexane as a fuel source (O'Connor, R. P., Klein, E. J., Schmidt, L. D., *Catalysis Letters,* 70:99 (2000)). These previous experiments did not use an evaporator mixer, as described herein. In these previous experiments the fuel was typically boiled and then mixed with air, and results could be provided because the hexane has a high auto-ignition temperature. Results for n-hexane were only obtained at 2.5 SLPM, and, typically, only a small amount of olefins could be produced. These previous results are compared with n-decane and n-hexadecane results of the present examples at 4 SLPM. The flow rates, though not identical, are comparable. It is believed that a higher flow rate would likely slightly increase the olefin production in hexane, but as hexane is less reactive than either n-decane and n-hexadecane, it is believed that increasing the flow rate would not significantly affect olefin production in hexane.

The conversion was observed to generally increase as the molecular weight of the fuel increased. While for $CH_4$ the conversion was typically 85 to 95%, depending on the C/O ratio and preheat temperature of the inlet gases used, for the higher hydrocarbons, that is hydrocarbons including at least 6 carbon atoms, the conversion was always greater than 99% for C/O ratios near 1, even beyond the syngas ratio of C/O=1. Similarly, the $O_2$ conversion was higher for the higher hydrocarbons at all C/O ratios. These results are believed to be qualitatively explained by the higher reactivities of larger hydrocarbons. The C—H bond energy is 104 kcal/mole for $CH_4$, while the C—C bond energy is 80 kcal/mole for linear alkanes.

The CO and $H_2$ selectivities shown in FIG. 14 are somewhat higher for n-hexane than for n-decane and n-hexadecane, with some of this difference believed to be caused by the large amounts of olefins produced from higher alkanes. It is noted that the $CO_2$ produced is nearly the same for all fuels reported in FIG. 10. It is about 10% and appears to be substantially independent of C/O, that is the selectivity is about 10% and does not change as the C/O ratio is varied.

The selectivities to α-olefins also increased with the molecular weight of the alkane, as shown in FIG. 14. No α-olefins were observed upon reacting methane, but a product mixture of up to about 5% by reacting hexane, about 60% by reacting decane, and about 80% by reacting hexadecane was observed (Hickman et al., *Science,* 259(5093):343 (1993); Hickman et al., *Catal. Lett.,* 17(3-4):223 (1993)). It is believed that methane clearly can form olefins only by coupling, which is difficult to do. The higher alkanes, however, can form olefins by cracking reactions. Therefore, the larger the alkane used as a reactant, the more fragment olefins are possible.

Increasing C/O also caused a transition in selectivities from ethylene to higher alkenes, as shown in FIG. 14. This seems reasonable in terms of the temperature and the series reactions, well known in the art, by which larger molecules decompose into smaller ones. All higher olefins produced by the present processes, using n-alkanes as the fuel, are α-olefins with double bonds only at one end of the hydrocarbon chain.

There were substantially no small alkanes formed by the present processes. The total alkane selectivity was less than 8% for all reactant fuels of the present examples. Furthermore, the total alkanes produced by the present processes were predominately $CH_4$, typically more than 95% of the alkanes observed. There were also substantially no branched isomers of alkanes or olefins observed in any of the products, indicating little isomerization even though reaction temperatures were typically maintained above 800° C.

Rates and Mechanisms

Without being held to any particular theory, it is believed, as a result of the above examples, that only a few dominant reaction pathways operate in these processes. The detailed chemistry of homogeneous combustion and pyrolysis for these alkanes is well known from diesel combustion and naphtha steam reforming applications. The detailed surface chemistry of methane and ethane partial oxidation on rhodium and platinum surfaces is also fairly well established, although the kinetics of surface reactions of higher alkanes has not yet been established.

The exact roles of the catalyst surface and homogeneous reaction steps, the elementary reaction occurring in the gas phase, are unclear in these experiments; however, it is believed that surface and homogeneous reactions are tightly coupled in this catalyst geometry because of the small channel sizes present in the ceramic foam monoliths preferably used in the present processes. While methane partial oxidation is known to be greater than about 90%, that is about 90% of the reactions occur on the catalyst surface and about 10% occur in the gas phase, ethane oxidative dehydrogenation occurs through both surface and homogeneous routes (Henning, D. A., Schmidt, L. D., Chem. Eng. Sci., 57(14):2615 (2002)). By analogy with $CH_4$ and $C_2H_6$ partial oxidation (Hickman, D. A., Schmidt, L. D., Science, 259:343 (1993); Bodke, A. S., et al., Science, 285:712 (1999)), it is believed that most CO and $CO_2$ formed by the present processes are formed by surface reactions on the catalyst surface and that most olefins are formed by homogeneous pyrolysis reactions, as described below.

It is also believed that reaction could also be occurring before, within, or after the catalyst, using the heat generated by the reactions on the catalyst surface. A preheat of about 250° C. for n-decane and about 400° C. for n-hexadecane is believed to cause negligible reaction in the residence time of about 20 ms in the preheat-mixing zone. However, the gases are heated to considerably higher temperatures before entering the porous catalyst by thermal diffusion of heat from the hot catalyst face, and homogeneous reaction may occur in the region within several millimeters of the catalyst. It is believed, however, that a substantial majority of the reaction occurs within the catalyst because reaction temperatures are highest within the catalyst, and heat conduction between gas and surface assures highest gas temperature will occur within the catalyst.

It is believed that reaction is substantially initiated at the surface near the entrance of the catalyst, where oxygen concentration and surface coverage are high. As the reaction temperature is highest in this zone, oxidation reactions go rapidly to completion and consume all $O_2$ within the first millimeter of entering the catalyst, presumably generating mostly CO, $CO_2$, $H_2$, and $H_2O$. Once all $O_2$ is reacted, pyrolysis reactions are believed to dominate, producing mostly olefins. These reactions could be homogeneous or on the surface, and it is, therefore, difficult to determine the roles of surface and homogeneous reactions from product distributions.

The pathway that is believed to explain olefins is that of initiation by pyrolysis of the parent alkane to produce two alkyl radicals:

$$R_1\text{-}R_2 \rightarrow R_1\cdot + R_2\cdot ,$$

with the fragments $R_1\cdot$ and $R_2\cdot$ determined by the statistical probability of C—C bond scission, accounting for the higher bond strengths associated with methyl and ethyl. Next, a radical can decompose by β scission to yield ethylene and a smaller radical:

$$RCH_2CH_2\cdot \rightarrow R\cdot + C_2H_4$$

or by β hydrogen elimination to yield a larger stable olefin:

$$RCH_2CH_2\cdot \rightarrow RC_2H\!=\!CH_2.$$

This process could continue with the radical eliminating ethylene molecules until it finally forms the ethyl or propyl radical, which can only dehydrogenate to form ethylene or propylene:

$$C_2H_5\cdot \rightarrow H\cdot + C_2H_4$$

$$C_3H_7\cdot \rightarrow H\cdot + C_3H_6$$

Thus the overall process is believed to be a series of reactions, such as:

$$\text{n-}C_{16}H_{34} \rightarrow 2\ \text{n-}C_8H_{17}\cdot \rightarrow \text{n-}C_6H_{13}\cdot \rightarrow \text{n-}C_4H_9\cdot \rightarrow C_2H_5\cdot \rightarrow C_2H_4$$

whose overall stoichiometry is:

$$\text{n-}C_{16}H_{34} \rightarrow 8C_2H_4.$$

If the hexadecane molecule dissociated initially to produce radicals with an odd number of carbon atoms, the overall reaction would give 5 ethylene and 2 propylene molecules:

$$\text{n-}C_{16}H_{34} \rightarrow 5\ C_2H_4 + 2\ C_3H_6.$$

This may account for the $C_2H_4/C_3H_6$ ratio of about 2:1 observed in the present examples. According to this, if C/O is increased, the resultant reaction temperature is lower, and β hydrogen elimination becomes more important, yielding a larger olefin from the alkyl fragment.

It is further believed that bimolecular hydrogen abstraction reactions:

$$R_1\cdot + R_2H \rightarrow R_1H + R_2\cdot.$$

where a radical reacts with a parent alkane to form an alkane and an alkyl radical of the parent, should not be important because it would produce smaller alkanes and also internal olefins when the alkyl eliminates a hydrogen atom. Since product including very little branched alkanes or olefins, was observed, it is believed that bimolecular alkyl transfer reactions must also be insignificant.

The complete disclosure of all patent, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention as defined by the claims.

We claim:

1. A process for the production of synthesis gas, the process comprising:
   providing a fuel source comprising at least one liquid hydrocarbon;
   providing at least one source of oxygen comprising molecular oxygen;
   delivering the fuel source to a reactor comprising a wall;
   forming a film of the fuel source on the reactor wall;
   contacting the fuel source with the source of oxygen;
   forming a vaporized mixture of the fuel source and the source of oxygen; and contacting the vaporized mixture of the fuel source and the source of oxygen with a catalyst under conditions effective to produce a reaction product comprising synthesis gas.

2. The process of claim 1 wherein the process is carried out under autothermal conditions.

3. The process of claim 1 wherein the vaporized mixture of the fuel source and the source of oxygen contacts the catalyst for at least about 5 milliseconds.

4. The process of claim 3 wherein the vaporized mixture of the fuel source and the source of oxygen contacts the catalyst for no greater than about 25 milliseconds.

5. The process of claim 1 wherein the liquid hydrocarbon comprises at least 6 carbon atoms.

6. The process of claim 1 wherein at least about 60 percent of the fuel source that is reacted forms synthesis gas.

7. The process of claim 1 wherein the catalyst comprises a metal disposed on a support, wherein the metal is selected from the group consisting of a Group VIII metal, a Group IB metal, tin, and combinations thereof.

8. The process of claim 7 wherein the metal comprises rhodium.

9. The process of claim 7 wherein the support is a ceramic foam monolith.

10. The process of claim 1 wherein carbon is present in the fuel source in an atomic ratio of at least about 0.3:1 carbon to oxygen.

11. The process of claim 10 wherein carbon is present in the fuel source in an atomic ratio of no greater than about 2:1 carbon to oxygen.

12. The process of claim 1 wherein the source of oxygen comprises air.

13. The process of claim 1 wherein the source of oxygen is pure $O_2$.

14. The process of claim 1 further comprising contacting the fuel source and the source of oxygen with water.

15. The process of claim 1 wherein the vaporized mixture of the fuel source and the source of oxygen contacts the catalyst at a flow rate of at least about 0.5 standard liters per minute.

16. The process of claim 15 wherein the vaporized mixture of the fuel source and the source of oxygen contacts the catalyst at a flow rate of no greater than about 20 standard liters per minute.

17. The process of claim 1 wherein the fuel source and the source of oxygen are vaporized and mixed substantially simultaneously.

18. The process of claim 17 wherein the mixture of the fuel source and the source of oxygen is heated to a temperature of at least about 25° C. above the boiling point of the fuel source prior to contacting the catalyst.

19. The process of claim 18 wherein the fuel source and the source of oxygen are heated to a temperature of no greater than about 150° C. above the boiling point of the fuel source prior to contacting the catalyst.

* * * * *